(12) United States Patent
Kuzma et al.

(10) Patent No.: US 8,784,865 B2
(45) Date of Patent: Jul. 22, 2014

(54) LONG TERM DRUG DELIVERY DEVICES WITH POLYURETHANE-BASED POLYMERS AND THEIR MANUFACTURE

(71) Applicant: Endo Pharmaceuticals Solutions Inc., Malvern, PA (US)

(72) Inventors: Petr Kuzma, Princeton, NJ (US); Harry Quandt, Bensalem, PA (US)

(73) Assignee: Endo Pharmaceuticals Solutions Inc., Malvern, PA (US)

( * ) Notice: Subject to any disclaimer, the term of this patent is extended or adjusted under 35 U.S.C. 154(b) by 0 days.

(21) Appl. No.: 13/892,946

(22) Filed: May 13, 2013

(65) Prior Publication Data

US 2014/0012222 A1    Jan. 9, 2014

Related U.S. Application Data

(63) Continuation of application No. 13/416,999, filed on Mar. 9, 2012, now Pat. No. 8,460,274, which is a continuation of application No. 12/912,655, filed on Oct. 26, 2010, now Pat. No. 8,303,977, which is a continuation of application No. 12/242,497, filed on Sep. 30, 2008, now Pat. No. 7,858,110.

(51) Int. Cl.
*A61F 2/00* (2006.01)
*A61K 9/00* (2006.01)

(52) U.S. Cl.
CPC ............. *A61K 9/0024* (2013.01); *A61K 9/0092* (2013.01)
USPC .................... 424/423; 606/194; 604/890.1

(58) Field of Classification Search
None
See application file for complete search history.

(56) References Cited

U.S. PATENT DOCUMENTS

| | | | |
|---|---|---|---|
| 3,948,254 A | 4/1976 | Zaffaroni |
| 3,975,350 A | 8/1976 | Hudgin |
| 3,993,073 A | 11/1976 | Zaffaroni |
| 4,131,604 A | 12/1978 | Szycher |
| 4,136,145 A | 1/1979 | Fuchs |
| 4,207,809 A | 6/1980 | Brill |
| 4,207,890 A | 6/1980 | Mamajek |
| 4,386,039 A | 5/1983 | Szycher |
| 4,469,671 A | 9/1984 | Zimmerman |
| 4,523,005 A | 6/1985 | Szycher |
| 4,743,673 A | 5/1988 | Johnston |
| 4,751,133 A | 6/1988 | Szycher |
| 4,933,182 A | 6/1990 | Hayashi |

(Continued)

FOREIGN PATENT DOCUMENTS

| | | |
|---|---|---|
| CN | 1863504 A | 11/2006 |
| CN | 101193626 A | 6/2008 |

(Continued)

OTHER PUBLICATIONS

U.S. Appl. No. 10/915,625, Final Office Action mailed Mar. 16, 2009.

(Continued)

*Primary Examiner* — Bethany Barham
(74) *Attorney, Agent, or Firm* — RatnerPrestia

(57) ABSTRACT

This invention is related to the use of polyurethane-based polymer as a drug delivery device to deliver biologically active compounds at a constant rate for an extended period of time and methods of manufactures thereof. The device is very biocompatible and biostable, and is useful as an implant in patients (humans and animals) for the delivery of appropriate bioactive substances to tissues or organs.

41 Claims, 16 Drawing Sheets

(56) References Cited

U.S. PATENT DOCUMENTS

| | | | |
|---|---|---|---|
| 5,035,891 | A | 7/1991 | Runkel |
| 5,207,705 | A | 5/1993 | Trudell |
| 5,254,662 | A | 10/1993 | Szycher |
| 5,266,325 | A | 11/1993 | Kuzma |
| 5,292,515 | A | 3/1994 | Moro |
| 5,354,835 | A | 10/1994 | Blair |
| 5,626,862 | A | 5/1997 | Brem |
| 5,629,008 | A | 5/1997 | Lee |
| 5,728,396 | A | 3/1998 | Peery |
| 5,756,632 | A | 5/1998 | Ward |
| 5,789,411 | A | 8/1998 | Gooberman |
| 5,958,317 | A | 9/1999 | Aguadisch et al. |
| 5,980,927 | A | 11/1999 | Nelson |
| 6,113,938 | A | 9/2000 | Chen |
| 6,287,295 | B1 | 9/2001 | Chen |
| 6,313,254 | B1 | 11/2001 | Meijs |
| 6,375,978 | B1 | 4/2002 | Kleiner |
| 7,067,116 | B1 | 6/2006 | Bess |
| 7,648,712 | B2 | 1/2010 | Bess |
| 7,858,110 | B2 | 12/2010 | Kuzma |
| 2001/0006677 | A1 | 7/2001 | McGinity |
| 2002/0028857 | A1 | 3/2002 | Holy |
| 2003/0153983 | A1 | 8/2003 | Miller |
| 2003/0170305 | A1 | 9/2003 | O'Neil |
| 2004/0002729 | A1 | 1/2004 | Zamore |
| 2004/0175428 | A1 | 9/2004 | Appel |
| 2005/0037078 | A1 | 2/2005 | Kuo |
| 2005/0202371 | A1 | 9/2005 | McGuire |
| 2006/0110428 | A1 | 5/2006 | deJuan |
| 2006/0204540 | A1 | 9/2006 | Kuzma |
| 2006/0204559 | A1 | 9/2006 | Bess |
| 2008/0004260 | A1 | 1/2008 | Singh |
| 2009/0098182 | A1 | 4/2009 | Kuzma |
| 2009/0208540 | A1 | 8/2009 | Quandt |
| 2010/0080835 | A1 | 4/2010 | Kuzma |
| 2010/0203104 | A1 | 8/2010 | De Graaff et al. |
| 2011/0059147 | A1 | 3/2011 | Kuo |
| 2011/0184376 | A1 | 7/2011 | Kuzma |

FOREIGN PATENT DOCUMENTS

| | | |
|---|---|---|
| EP | 0200224 A2 | 11/1986 |
| EP | 0241178 A1 | 10/1987 |
| EP | 1660034 A2 | 5/2006 |
| EP | 1982695 A2 | 10/2008 |
| JP | 10076016 A | 3/1998 |
| JP | 2007-502139 A | 2/2007 |
| WO | WO-0143726 A1 | 6/2001 |
| WO | WO-0170194 A1 | 9/2001 |
| WO | WO-2005013936 A2 | 2/2005 |
| WO | WO-2006078320 A2 | 7/2006 |
| WO | WO-2006099288 A3 | 9/2006 |
| WO | WO-2008070118 A1 | 6/2008 |
| WO | WO-2009158415 A1 | 12/2009 |
| WO | WO-2010039641 A2 | 4/2010 |
| WO | WO-2010039717 A1 | 4/2010 |
| WO | WO-2010039722 A1 | 4/2010 |

OTHER PUBLICATIONS

U.S. Appl. No. 10/915,625, Final Office Action mailed Mar. 31, 2010.
U.S. Appl. No. 10/915,625, Non Final Office Action mailed Sep. 7, 2007.
U.S. Appl. No. 10/915,625, Non Final Office Action mailed Sep. 29, 2009.
U.S. Appl. No. 10/915,625, Notice of Allowance mailed Jul. 6, 2010.
U.S. Appl. No. 12/242,497, Non Final Office Action mailed Feb. 3, 2010.
U.S. Appl. No. 12/242,497, Notice of Allowance mailed Sep. 16, 2010.
U.S. Appl. No. 12/351,617, Non Final Office Action mailed Dec. 8, 2010.
U.S. Appl. No. 12/569,558, Non Final Office Action mailed Nov. 8, 2011.
U.S. Appl. No. 12/873,130, Non Final Office Action mailed Oct. 4, 2011.
U.S. Appl. No. 12/873,130, Notice of Allowance mailed Feb. 27, 2012, 17 pgs.
U.S. Appl. No. 12/873,130, Notice of Allowance mailed Sep. 25, 2012, 10 pgs.
U.S. Appl. No. 12/907,717, Non Final Office Action mailed Feb. 27, 2012, 10 pgs.
U.S. Appl. No. 12/907,717, Notice of Allowance mailed Jun. 8, 2012, 7 pgs.
U.S. Appl. No. 12/907,717, Notice of Allowance mailed Aug. 29, 2012, 7 pgs.
U.S. Appl. No. 12/915,625, Non Final Office Action mailed Sep. 29, 2009.
U.S. Appl. No. 13/121,152, Non Final Office Action mailed Dec. 27, 2012, 18 pgs.
U.S. Appl. No. 13/416,999, Non Final Office Action mailed Sep. 14, 2012, 21 pgs.
U.S. Appl. No. 13/416,999, Notice of Allowance mailed Feb. 14, 2013, 22 pgs.
Chinese Application Serial No. 200480029342.0, Office Action dated Sep. 21, 2007.
Chinese Application Serial No. 200480029342.0, Office Action dated Nov. 27, 2009.
Chinese Application Serial No. 200980142114.7, Office Action dated Feb. 28, 2013.
"Design of a Polyurethane Membrane for the Encapsulation of Islets of Langerhans", Biomaterials, vol. 13, No. 3 (1992), 136-144.
European Application Serial No. 08010973, European Search Report dated Apr. 27, 2010.
Hsu, "Plasma-Induced Graft Polymerization of L-Lactide on Polyurethane", 24th Annual Mtg. Soc. Biomat, San Diego, CA (Apr. 22-26, 1998).
Indian Application Serial No. 282/MUMNP/2006, First Examination Report received Aug. 4, 2008.
International Application Serial No. PCT/US2009/058571, International Search Report and Written Opinion dated May 31, 2010.
International Application Serial No. PCT/US2009/058571, International Search Report dated May 25, 2010.
International Application Serial No. PCT/US2009/058571, International Written Opinion dated May 25, 2010.
International Application Serial No. PCT/US2009/058578, International Search Report and Written Opinion mailed Feb. 2, 2010.
International Application Serial No. PCT/US2009/058801, International Search Report and Written Opinion dated Feb. 5, 2010.
International Application Serial No. PCT/US2009/058810, International Search Report and Written Opinion dated Feb. 3, 2010.
International Application Serial No. PCT/US2009/059012, International Search Report and Written Opinion mailed Dec. 17, 2009.
Israel Application Serial No. 211953, Notice of Defect mailed May 26, 2013, 1 pg.
Japanese Application Serial No. 2011-031294, Notice of Reason for Refusal dated Oct. 11, 2011.
Japanese Application Serial No. 2011-031294, Notice of Defect mailed May 28, 2013, 1 pg. (No English Translation).
Mexican Application Serial No. PA/a/2006-001612, Office Action dated Jan. 18, 2010.
Mexican Application Serial No. PA/a/2006-001612, Office Action dated Jan. 20, 2009.
Mexican Application Serial No. PA/a/2006-001612, Office Action dated Jul. 22, 2009.
Mexican Application Serial No. PA/a/2006-001612, Office Action dated Jul. 25, 2008.
"Polyurethane Composites for Medical Applications", Advances in Plastics Technology, International Conference, 5th, Katowice, Poland (Nov. 4-6, 2003) Abstract only, (Nov. 4, 2006), 1 pg.
"Polyurethanes", Encyclopedia of Polymer Science and Technology, John Wiley & Sons (2002), 3 pgs.
"Remington: The Science and Practice of Pharmacy", A.R. Genaro Editor, Mack Publishing (1995).
Russian Application Serial No. 2011117328, Office Action dated Apr. 15, 2013.

(56) References Cited

OTHER PUBLICATIONS

Ukraine Application Serial No. a201105431, Office Action dated Mar. 21, 2013.
Japanese Office Action mailed Nov. 12, 2013 for corresponding Japanese Application No. JP 2011-529355, including English language translation.
Mexican Office Action mailed Oct. 7, 2013 for corresponding Mexican Application No. MX/a/2012/006029.
Japanese Office Action mailed Nov. 12, 2013 for corresponding Japanese Application No. JP 2011-529360, including English language translation.
European Summons to attend oral proceedings pursuant to Rule 115(1) EPC mailed Oct. 21, 2013 for corresponding European Patent Application No. 08010973.9.
Chinese Office Action mailed Oct. 21, 2013 for corresponding Chinese Patent Application No. 200980142114.7, including English language translation.
Translation of Ukraine Office Action mailed Dec. 3, 2013 for corresponding Ukrainian Application No. a201105432.
Russian Official Action for Application No. 2011117327, dated Sep. 18, 2013.
The State Intellectual Property Office of the People's Republic of China Office Action for Application No. 200980142113.2 dated Jul. 17, 2013 (with English translation).
Ukrainian Official Action for Application No. a201105430 dated Apr. 12, 2013 (with English translation).
US Office Action for U.S. Appl. No. 13/121,152 mailed Oct. 9, 2013.
US Notice of Allowance for U.S. Appl. No. 13/952,327 mailed Oct. 11, 2013.
Israel Ministry of Justice Patent Office, Notification of Defects in Patent Application No. 211954, dated Dec. 22, 2013.
English Translation of the Office Action Issued for Israeli Patent Application No. 211952 on Dec. 18, 2013.
Japanese Office Action Issued for Application No. 2011-529306 Dated Dec. 3, 2013.
Japanese Office Action for Application No. 2011-529306 dated Apr. 1, 2014.

ns, artificial tendons, arteries and veins. Formulations for delivery of active agents using polyurethane implantable devices, however, require a liquid medium or carrier for the diffusion of the drug at a zero order rate.

LONG TERM DRUG DELIVERY DEVICES WITH POLYURETHANE-BASED POLYMERS AND THEIR MANUFACTURE

CROSS-REFERENCES TO RELATED APPLICATIONS

This application is a Continuation of U.S. patent application Ser. No. 13/416,999, filed Mar. 9, 2012, which is a Continuation of U.S. patent application Ser. No. 12/912,655, filed Oct. 26, 2010, which is a Continuation of U.S. patent application Ser. No. 12/242,497, filed Sep. 30, 2008, the contents of which are incorporated herein by reference in their entirety.

BACKGROUND

Due to its excellent biocompatibility, biostability and physical properties, polyurethane or polyurethane-containing polymers have been used to fabricate a large number of implantable devices, including pacemaker leads, artificial hearts, heart valves, stent coverings, artificial tendons, arteries and veins. Formulations for delivery of active agents using polyurethane implantable devices, however, require a liquid medium or carrier for the diffusion of the drug at a zero order rate.

SUMMARY

Described herein are methods and compositions based on the unexpected discovery that solid formulations comprising one or more active agents can be used at the core of a polyurethane implantable device such that the active agent is released in a controlled-release, zero-order manner from the implantable device. The active agents and polyurethane coating can be selected based on various physical parameters, and then the release rate of the active from the implantable device can be optimized to a clinically-relevant release rate based on clinical and/or in vitro trials.

One embodiment is directed to a method for delivering an active agent in a subject, comprising: implanting an implantable device into the subject, wherein the implantable device comprises an active agent surrounded by a polyurethane-based polymer, wherein the polyurethane-based polymer is selected according to one or more physical properties that allow for optimized release of the active agent from the implantable device after implantation into the subject. In a particular embodiment, the implantable device further comprising one or more pharmaceutically acceptable carriers. In a particular embodiment, the polyurethane-based polymer is selected based on its equilibrium water content or flex modulus. In a particular embodiment, the polyurethane-based polymer is selected based on the molecular weight of the active agent.

One embodiment is directed to a drug delivery device for the controlled release of at least one active agent over an extended period of time to produce local or systemic pharmacological effects, comprising: a) a polyurethane-based polymer formed to define a hollow space, wherein the polyurethane-based polymer comprises one or more functional groups selected from the group consisting of: hydrophilic pendant groups, hydrophobic pendant groups, and mixtures thereof, and wherein the functional groups determine the degree to which the polymer is hydrophobic or hydrophilic; and b) a solid drug formulation comprising at least one active agent and optionally one or more pharmaceutically acceptable carriers, wherein the solid drug formulation is in the hollow space of the cylindrically shaped reservoir, and wherein the polymer properties and the water solubility characteristics of the at least one active agent are chosen to provide a desired release rate of the active agent from the device after implantation. In a particular embodiment, the drug delivery device is conditioned and primed under conditions chosen to match the water solubility characteristics of the at least one active agent. In a particular embodiment, the conditioning and priming conditions include the use of an aqueous medium (e.g., a saline solution) when the at least one active agent is hydrophilic. In a particular embodiment, the conditioning and priming conditions include the use of a hydrophobic medium (e.g., an oil-based medium) when the at least one active agent is hydrophobic. In a particular embodiment, the at least one active agent is selected from the group consisting of: drugs that can act on the central nervous system, psychic energizers, tranquilizers, anti-convulsants, muscle relaxants, anti-parkinson agents, analgesics, anti-inflammatory agents, anesthetics, antispasmodics, muscle contractants, anti-microbials, anti-malarials, hormonal agents, sympathomimetics, cardiovascular agents, diuretics and antiparasitic agents. In a particular embodiment, the hydrophilic pendant groups are selected from the group consisting of: ionic, carboxyl, ether and hydroxyl groups. In a particular embodiment, the hydrophobic pendant groups are selected from the group consisting of: alkyl and siloxane groups. In a particular embodiment, the solid drug formulation comprises a pharmaceutically acceptable carrier (e.g., stearic acid). In a particular embodiment, the polyurethane-based polymer is thermoplastic polyurethane or thermoset polyurethane. In a particular embodiment, the thermoplastic polyurethane comprises macrodiols, diisocyanates, difunctional chain extenders or mixtures thereof. In a particular embodiment, the thermoset polyurethane comprises multifunctional polyols, isocyanates, chain extenders or mixtures thereof. In a particular embodiment, the thermoset polyurethane comprises a polymer chain that contains unsaturated bonds, and wherein appropriate crosslinkers and/or initiators are used to crosslink polymer subunits. In a particular embodiment, the appropriate conditioning and priming parameters can be selected to establish the desired delivery rates of the at least one active agent, wherein the priming parameters are time, temperature, conditioning medium and priming medium.

BRIEF DESCRIPTION OF THE DRAWINGS

FIG. 9A shows sections from the beginning, middle and end of a section of tubing. Elution was performed in a water bath or orbital shaker.
FIG. 9B is a graph of the release rate of risperidone from Carbothane® PC-3575A polyurethane implants (Flex Modulus 620 psi) prepared from tubing sections representing the beginning, middle and end of a coil of tubing as part of an assessment of the uniformity of the material within a particular lot. Samples were evaluated weekly for one year for elution using a water bath. All implants were of equivalent geometry and drug load.

FIG. 11B is a graph of the release rate of risperidone from Tecophilic® HP-60D-20 polyurethane implants (EWC, 14.9%) alone, sampled weekly for 15 weeks.

DETAILED DESCRIPTION

Figure 1:
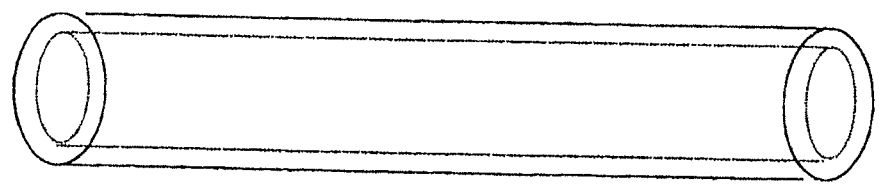
FIG. 1 is a side view of an implant with two open ends.

To take the advantage of the excellent properties of polyurethane-based polymers, the present invention is directed to the use of polyurethane-based polymers as drug delivery devices for releasing drugs at controlled rates for an extended period of time to produce local or systemic pharmacological effects. The drug delivery device can comprise a cylindrically-shaped reservoir surrounded by polyurethane-based polymer that controls the delivery rate of the drug inside the reservoir. The reservoir contains a formulation, e.g., a solid formulation, comprising one or more active ingredients and, optionally, pharmaceutically acceptable carriers. The carriers are formulated to facilitate the diffusion of the active ingredients through the polymer and to ensure the stability of the drugs inside the reservoir.

A polyurethane is any polymer consisting of a chain of organic units joined by urethane links. Polyurethane polymers are formed by reacting a monomer containing at least two isocyanate functional groups with another monomer containing at least two alcohol groups in the presence of a catalyst. Polyurethane formulations cover an extremely wide range of stiffness, hardness, and densities.

generalized polyurethane reaction

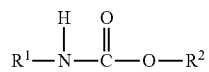

Polyurethanes are in the class of compounds called "reaction polymers," which include epoxies, unsaturated polyesters and phenolics. A urethane linkage is produced by reacting an isocyanate group, —N=C=O with a hydroxyl (alcohol) group, —OH. Polyurethanes are produced by the polyaddition reaction of a polyisocyanate with a polyalcohol (polyol) in the presence of a catalyst and other additives. In this case, a polyisocyanate is a molecule with two or more isocyanate functional groups, $R—(N=C=O)_{n\geq 2}$ and a polyol is a molecule with two or more hydroxyl functional groups, $R'—(OH)_{n\geq 2}$. The reaction product is a polymer containing the urethane linkage, —RNHCOOR'—. Isocyanates react with any molecule that contains an active hydrogen. Importantly, isocyanates react with water to form a urea linkage and carbon dioxide gas; they also react with polyetheramines to fowl polyureas.

Polyurethanes are produced commercially by reacting a liquid isocyanate with a liquid blend of polyols, catalyst, and other additives. These two components are referred to as a polyurethane system, or simply a system. The isocyanate is commonly referred to in North America as the "A-side" or just the "iso," and represents the rigid backbone (or "hard segment") of the system. The blend of polyols and other additives is commonly referred to as the "B-side" or as the "poly," and represents the functional section (or "soft segment") of the system. This mixture might also be called a "resin" or "resin blend." Resin blend additives can include chain extenders, cross linkers, surfactants, flame retardants, blowing agents, pigments and fillers. In drug delivery applications, the "soft segments" represent the section of the polymer that imparts the characteristics that determine the diffusivity of an active pharmaceutical ingredient (API) through that polymer.

The elastomeric properties of these materials are derived from the phase separation of the hard and soft copolymer segments of the polymer, such that the urethane hard segment domains serve as cross-links between the amorphous polyether (or polyester) soft segment domains. This phase separation occurs because the mainly non-polar, low-melting soft segments are incompatible with the polar, high-melting hard segments. The soft segments, which are formed from high molecular weight polyols, are mobile and are normally present in coiled formation, while the hard segments, which are formed from the isocyanate and chain extenders, are stiff and immobile. Because the hard segments are covalently coupled to the soft segments, they inhibit plastic flow of the polymer chains, thus creating elastomeric resiliency. Upon mechanical deformation, a portion of the soft segments are stressed by uncoiling, and the hard segments become aligned in the stress direction. This reorientation of the hard segments and consequent powerful hydrogen-bonding contributes to high tensile strength, elongation, and tear resistance values.

The polymerization reaction is catalyzed by tertiary amines, such as, for example, dimethylcyclohexylamine, and organometallic compounds, such as, for example, dibutyltin dilaurate or bismuth octanoate. Furthermore, catalysts can be chosen based on whether they favor the urethane (gel) reaction, such as, for example, 1,4-diazabicyclo[2.2.2]octane (also called DABCO or TEDA), or the urea (blow) reaction, such as bis-(2-dimethylaminoethyl)ether, or specifically drive the isocyanate trimerization reaction, such as potassium octoate.

Polyurethane polymer formed by reacting a diisocyanate with a polyol

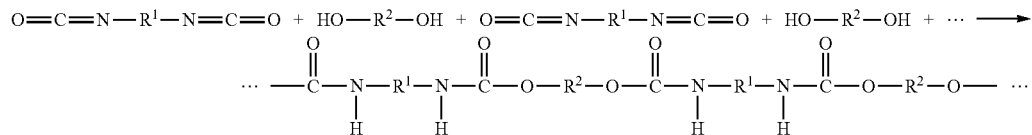

Isocyanates with two or more functional groups are required for the formation of polyurethane polymers. Volume wise, aromatic isocyanates account for the vast majority of global diisocyanate production. Aliphatic and cycloaliphatic isocyanates are also important building blocks for polyurethane materials, but in much smaller volumes. There are a number of reasons for this. First, the aromatically-linked isocyanate group is much more reactive than the aliphatic one. Second, aromatic isocyanates are more economical to use. Aliphatic isocyanates are used only if special properties are required for the final product. Light stable coatings and elastomers, for example, can only be obtained with aliphatic isocyanates. Aliphatic isocyanates also are favored in the production of polyurethane biomaterials due to their inherent stability and elastic properties.

Examples of aliphatic and cycloaliphatic isocyanates include, for example, 1,6-hexamethylene diisocyanate (HDI), 1-isocyanato-3-isocyanatomethyl-3,5,5-trimethyl-cyclohexane (isophorone diisocyanate, IPDI) and 4,4'-diisocyanato dicyclohexylmethane ($H_{12}$MDI). They are used to produce light stable, non-yellowing polyurethane coatings and elastomers. $H_{12}$MDI prepolymers are used to produce high performance coatings and elastomers with optical clarity and hydrolysis resistance. Tecoflex®, Tecophilic® and Carbothane® polyurethanes are all produced from $H_{12}$MDI prepolymers.

Polyols are higher molecular weight materials manufactured from an initiator and monomeric building blocks and, where incorporated into polyurethane systems, represent the "soft segments" of the polymer. They are most easily classified as polyether polyols, which are made by the reaction of epoxides (oxiranes) with an active hydrogen containing starter compounds, or polyester polyols, which are made by the polycondensation of multifunctional carboxylic acids and hydroxyl compounds.

Tecoflex® polyurethanes and Tecophilic® polyurethanes are cycloaliphatic polymers and are of the types produced from polyether-based polyols. For the Tecoflex® polyurethanes, the general structure of the polyol segment is represented as,

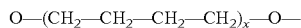

whereby an increase in "x" represents a increase in flexibility (decreased "Flex Modulus"; "FM"), yielding FM ranging from about 1000-92,000 psi. From the standpoint of drug release from these materials, the release of a relatively hydrophobic API decreases as the FM increases.

For the Tecophilic® (hydrophilic) polyurethanes, the general structure of the polyol segment is represented as,

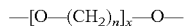

whereby increases in "n" and "x" represent variations in hydrophilicity, and yield equilibrium water contents (% EWC) ranging from about 5%-43%. From the standpoint of drug release from these materials, the release of a relatively hydrophilic API increases as the % EWC increases.

Specialty polyols include, for example, polycarbonate polyols, polycaprolactone polyols, polybutadiene polyols, and polysulfide polyols.

Carbothane® polyurethanes are cycloaliphatic polymers and are of the types produced from polycarbonate-based polyols. The general structure of the polyol segment is represented as, O—[(CH$_2$)$_6$—CO$_3$]$_n$—(CH$_2$)—O— whereby an increase in "n" represents a increase in flexibility (decreased FM), yielding FM ranging from about 620-92,000 psi. From the standpoint of drug release from these materials, the release of a relatively hydrophobic API will decrease as the FM increases.

Chain extenders and cross linkers are low molecular weight hydroxyl- and amine-terminated compounds that play an important role in the polymer morphology of polyurethane fibers, elastomers, adhesives and certain integral skin and microcellular foams. Examples of chain extenders include, for example, ethylene glycol, 1,4-butanediol (1,4-BDO or BDO), 1,6-hexanediol, cyclohexane dimethanol and hydroquinone bis(2-hydroxyethyl)ether (HQEE). All of these glycols form polyurethanes that phase separate well, farm well-defined hard segment domains, and are melt processable. They are all suitable for thermoplastic polyurethanes with the exception of ethylene glycol, since its derived bis-phenyl urethane undergoes unfavorable degradation at high hard segment levels. Tecophilic®, Tecoflex® and Carbothane® polyurethanes all incorporate the use of 1,4-butanediol as the chain extender.

The current invention provides a drug delivery device that can achieve the following objectives: a controlled-release rate (e.g., zero-order release rate) to maximize therapeutic effects and minimize unwanted side effects, an easy way to retrieve the device if it is necessary to end the treatment, an increase in bioavailability with less variation in absorption and no first pass metabolism.

The release rate of the drug is governed by the Fick's Law of Diffusion as applied to a cylindrically shaped reservoir device (cartridge). The following equation describes the relationship between different parameters:

$$\frac{dM}{dt} = \frac{2\pi h p \Delta C}{\ln(r_o/r_i)}$$

where:
dM/dt: drug release rate;
h: length of filled portion of device;
ΔC: concentration gradient across the reservoir wall;
$r_o/r_i$: ratio of outside to inside radii of device; and
p: permeability coefficient of the polymer used.

The permeability coefficient is primarily regulated by the hydrophilicity or hydrophobicity of the polymer, the structure of the polymer, and the interaction of drug and the polymer. Once the polymer and the active ingredient are selected, p is a constant, h, $r_o$, and $r_i$ are fixed and kept constant once the cylindrically-shaped device is produced. ΔC is maintained constant.

To keep the geometry of the device as precise as possible, the device, e.g., a cylindrically-shaped device, can be manufactured through precision extrusion or precision molding process for thermoplastic polyurethane polymers, and reaction injection molding or spin casting process for thermosetting polyurethane polymers.

The cartridge can be made with either one end closed or both ends open. The open end can be plugged with, for example, pre-manufactured end plug(s) to ensure a smooth end and a solid seal, or, in the case of thermoplastic polyurethanes, by using heat-sealing techniques known to those skilled in the art. The solid actives and carriers can be compressed into pellet form to maximize the loading of the actives.

To identify the location of the implant, radiopaque material can be incorporated into the delivery device by inserting it into the reservoir or by making it into end plug to be used to seal the cartridge.

Once the cartridges are sealed on both ends with the filled reservoir, they are optionally conditioned and primed for an appropriate period of time to ensure a constant delivery rate.

The conditioning of the drug delivery devices involves the loading of the actives (drug) into the polyurethane-based polymer that surrounds the reservoir. The priming is done to stop the loading of the drug into the polyurethane-based polymer and thus prevent loss of the active before the actual use of the implant. The conditions used for the conditioning and priming step depend on the active, the temperature and the medium in which they are carried out. The conditions for the conditioning and priming may be the same in some instances.

The conditioning and priming step in the process of the preparation of the drug delivery devices is done to obtain a determined rate of release of a specific drug. The conditioning and priming step of the implant containing a hydrophilic drug can be carried out in an aqueous medium, e.g., in a saline solution. The conditioning and priming step of a drug delivery device comprising a hydrophobic drug is usually carried out in a hydrophobic medium such as, for example, an oil-based medium. The conditioning and priming steps can be carried out by controlling three specific factors, namely the temperature, the medium and the period of time.

A person skilled in the art would understand that the conditioning and priming step of the drug delivery device is affected by the medium in which the device is placed. A hydrophilic drug can be conditioned and primed, for example, in an aqueous solution, e.g., in a saline solution. Histrelin and Naltrexone implants, for example, have been conditioned and primed in saline solution, more specifically, conditioned in saline solution of 0.9% sodium content and primed in saline solution of 1.8% sodium chloride content.

The temperature used to condition and prime the drug delivery device can vary across a wide range of temperatures, e.g., about 37° C.

The time period used for the conditioning and priming of the drug delivery devices can vary from about a single day to several weeks depending on the release rate desired for the specific implant or drug. The desired release rate is determined by one of skill in the art with respect to the particular active agent used in the pellet formulation.

A person skilled in the art will understand the steps of conditioning and priming the implants are to optimize the rate of release of the drug contained within the implant. As such, a shorter time period spent on the conditioning and the priming of a drug delivery device results in a lower rate of release of the drug compared to a similar drug delivery device that has undergone a longer conditioning and priming step.

The temperature in the conditioning and priming step will also affect the rate of release in that a lower temperature results in a lower rate of release of the drug contained in the drug delivery device when compared to a similar drug delivery device that has undergone a treatment at a higher temperature.

Similarly, in the case of aqueous solutions, e.g., saline solutions, the sodium chloride content of the solution determines what type of rate of release will be obtained for the drug delivery device. More specifically, a lower content of sodium chloride results in a higher rate of release of drug when compared to a drug delivery device that has undergone a conditioning and priming step where the sodium chloride content was higher.

The same conditions apply for hydrophobic drugs where the main difference in the conditioning and priming step is that the conditioning and priming medium is a hydrophobic medium, more specifically an oil-based medium.

The drug (actives) that can be delivered include drugs that can act on the central nervous system, psychic energizers, tranquilizers, anti-convulsants, muscle relaxants, anti-parkinson, analgesic, anti-inflammatory, anesthetic, antispasmodic, muscle contractants, anti-microbials, anti-malarials, hormonal agents, sympathomimetic, cardiovascular, diuretics, antiparasitic and the like. Drugs also include drugs for use in urology, e.g., to treat or prevent a urological disorder or for contraception, such as, but not limited to, valrubicin, doxorubicin, bladder cancer cytotoxic agents, 5-amino salycilic acid (5-ASA), hydrocortisone, dexamethasone, anti-inflammatory agents, trospium chloride, tamsulosin, oxybutinin, and any hormone (such as, for example, ethinyl estradiol, levonorgestrel, estradiol, testosterone, and the like). Urological uses include, but are not limited to, for example, bladder cancer, interstitial cystitis, bladder inflammation, overactive bladder, benign prostatic hyperplasia (BPH), contraception, post-menopausal symptoms and hypogonatism. Implantable devices for use in bladder can range in size from, for example, about 2 mm to about 10 mm, from about 3 mm to about 6 mm, or about 2.7 mm in diameter and up to about 50 mm in length.

The current invention focuses on the application of polyurethane-based polymers, thermoplastics or thermosets, to the creation of implantable drug devices to deliver biologically active compounds at controlled rates for prolonged period of time. Polyurethane polymers can be made into, for example, cylindrical hollow tubes with one or two open ends through extrusion, (reaction) injection molding, compression molding, or spin-casting (see e.g., U.S. Pat. Nos. 5,266,325 and 5,292,515), depending on the type of polyurethane used.

Thermoplastic polyurethane can be processed through extrusion, injection molding or compression molding. Thermoset polyurethane can be processed through reaction injection molding, compression molding, or spin-casting. The dimensions of the cylindrical hollow tube should be as precise as possible.

Polyurethane-based polymers are synthesized from multifunctional polyols, isocyanates and chain extenders. The characteristics of each polyurethane can be attributed to its structure.

Thermoplastic polyurethanes are made of macrodiols, diisocyanates, and difunctional chain extenders (e.g., U.S. Pat. Nos. 4,523,005 and 5,254,662). Macrodiols make up the soft domains. Diisocyanates and chain extenders make up the hard domains. The hard domains serve as physical crosslinking sites for the polymers. Varying the ratio of these two domains can alter the physical characteristics of the polyurethanes, e.g., the flex modulus.

Thermoset polyurethanes can be made of multifunctional (greater than difunctional) polyols and/or isocyanates and/or chain extenders (e.g., U.S. Pat. Nos. 4,386,039 and 4,131,604). Thermoset polyurethanes can also be made by introducing unsaturated bonds in the polymer chains and appropriate crosslinkers and/or initiators to do the chemical crosslinking (e.g., U.S. Pat. No. 4,751,133). By controlling the amounts of crosslinking sites and how they are distributed, the release rates of the actives can be controlled.

Different functional groups can be introduced into the polyurethane polymer chains through the modification of the backbones of polyols depending on the properties desired. Where the device is used for the delivery of water soluble drugs, hydrophilic pendant groups such as ionic, carboxyl, ether, and hydroxy groups are incorporated into the polyols to increase the hydrophilicity of the polymer (e.g., U.S. Pat. Nos. 4,743,673 and 5,354,835). Where the device is used for the delivery of hydrophobic drugs, hydrophobic pendant groups such as alkyl, siloxane groups are incorporated into the polyols to increase the hydrophobicity of the polymer (e.g., U.S. Pat. No. 6,313,254). The release rates of the actives can also be controlled by the hydrophilicity/hydrophobicity of the polyurethane polymers.

For thermoplastic polyurethanes, precision extrusion and injection molding are the preferred choices to produce two open-end hollow tubes (FIG. 1) with consistent physical dimensions. The reservoir can be loaded freely with appropriate formulations containing actives and carriers or filled with pre-fabricated pellets to maximize the loading of the actives. One open end needs to be sealed first before the loading of the formulation into the hollow tube. To seal the two open ends, two pre-fabricated end plugs (FIG. 2) can be used. The sealing step can be accomplished through the application of heat or solvent or any other means to seal the ends, preferably permanently.

For thermoset polyurethanes, precision reaction injection molding or spin casting is the preferred choice depending on the curing mechanism. Reaction injection molding is used if the curing mechanism is carried out through heat and spin casting is used if the curing mechanism is carried out through light and/or heat. Hollow tubes with one open end (FIG. 3), for example, can be made by spin casting. Hollow tubes with two open ends, for example, can be made by reaction injection molding. The reservoir can be loaded in the same way as the thermoplastic polyurethanes.

To seal an open end, an appropriate light-initiated and/or heat-initiated thermoset polyurethane formulation can be used to fill the open end, and this is cured with light and/or heat. A pre-fabricated end plug, for example, can also be used to seal the open end by applying an appropriate light-initiated and/or heat-initiated thermoset polyurethane formulation on to the interface between the pre-fabricated end plug and the open end, and curing it with the light and/or heat or any other means to seal the ends, preferably permanently.

The final process involves the conditioning and priming of the implants to achieve the delivery rates required for the actives. Depending upon the types of active ingredient, hydrophilic or hydrophobic, the appropriate conditioning and priming media is chosen. Water-based media are preferred for hydrophilic actives, and oil-based media are preferred for hydrophobic actives.

As a person skilled in the art would readily know many changes can be made to the preferred embodiments of the invention without departing from the scope thereof. It is intended that all matter contained herein be considered illustrative of the invention and not it a limiting sense.

EXEMPLIFICATION

Example 1

Figure 2:
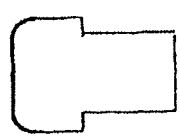
FIG. 2 is a side view of pre-fabricated end plugs used to plug the implants.
Figure 2:
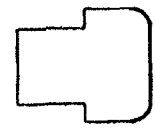
Figure 3:
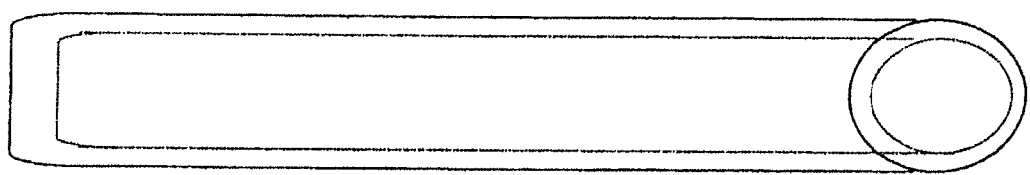
FIG. 3 is a side view of an implant with one open end.

Tecophilic® polyurethane polymer tubes are supplied by Thermedics Polymer Products and manufactured through a precision extrusion process. Tecophilic® polyurethane is a family of aliphatic polyether-based thermoplastic polyurethane that can be formulated to different equilibrium water contents (EWC) of up to 150% of the weight of dry resin. Extrusion grade formulations are designed to provide maximum physical properties of thermoformed tubing or other components. An exemplary tube and end cap structures are depicted in FIGS. 1-3.

The physical data for the polymers is provided below as made available by Thermedics Polymer Product (tests conducted as outlined by American Society for Testing and Materials (ASTM), Table 1).

TABLE 1

Tecophilic ® Typical Physical Test Data

| | ASTM | HP-60D-20 | HP-60D-35 | HP-60D-60 | HP-93A-100 |
|---|---|---|---|---|---|
| Durometer (Shore Hardness) | D2240 | 43D | 42D | 41D | 83A |
| Spec Gravity | D792 | 1.12 | 1.12 | 1.15 | 1.13 |
| Flex Modulus (psi) | D790 | 4,300 | 4,000 | 4,000 | 2,900 |
| Ultimate Tensile Dry (psi) | D412 | 8,900 | 7,800 | 8,300 | 2,200 |
| Ultimate Tensile Wet (psi) | D412 | 5,100 | 4,900 | 3,100 | 1,400 |
| Elongation Dry (%) | D412 | 430 | 450 | 500 | 1,040 |
| Elongation Wet (%) | D412 | 390 | 390 | 300 | 620 |

Figure 4:
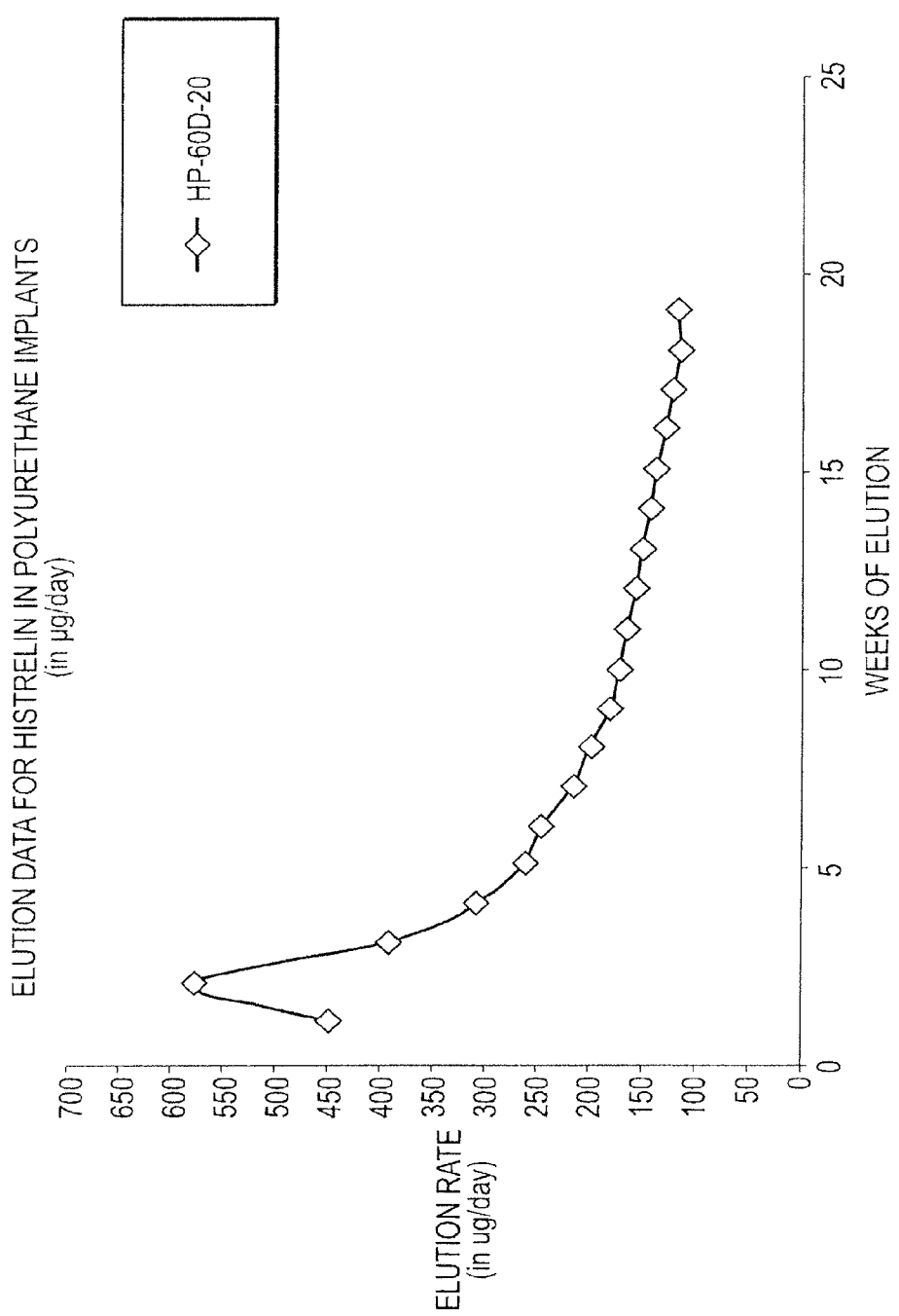
FIG. 4 is a graph of the elution rate of histrelin using an implant.

HP-60D-20 is extruded to tubes with thickness of 0.30 mm with inside diameter of 1.75 mm. The tubes are then cut into 25 mm in length. One side of the tube is sealed with heat using a heat sealer. The sealing time is less than one minute. Four pellets of histrelin acetate are loaded into the tube. Each pellet weighs approximately 13.5 mg for a total of 54 mg. Each pellet is comprised of a mixture of 98% histrelin and 2% stearic acid. The second end open of the tube is sealed with heat in the same way as for the first end. The loaded implant is then conditioned and primed. The conditioning takes place at room temperature in a 0.9% saline solution for one day. Upon completion of the conditioning, the implant undergoes priming. The priming takes place at room temperatures in a 1.8% saline solution for one day. Each implant is tested in vitro in a medium selected to mimic the pH found in the human body. The temperature of the selected medium was kept at approximately 37° C. during the testing. The release rates are shown on FIG. 4 and Table 2.

TABLE 2

Histrelin Elution Rates

| WEEKS OF ELUTION | HP-60D-20 (µg/day) |
|---|---|
| 1 | 451.733 |
| 2 | 582.666 |
| 3 | 395.9 |
| 4 | 310.29 |
| 5 | 264.92 |
| 6 | 247.17 |
| 7 | 215.93 |
| 8 | 201.78 |
| 9 | 183.22 |
| 10 | 174.99 |
| 11 | 167.72 |
| 12 | 158.37 |
| 13 | 153.95 |
| 14 | 146.46 |
| 15 | 139.83 |

TABLE 2-continued

Histrelin Elution Rates

| WEEKS OF ELUTION | HP-60D-20 (μg/day) |
|---|---|
| 16 | 129.6 |
| 17 | 124.46 |
| 18 | 118.12 |
| 19 | 120.35 |

Example 2

Figure 5:
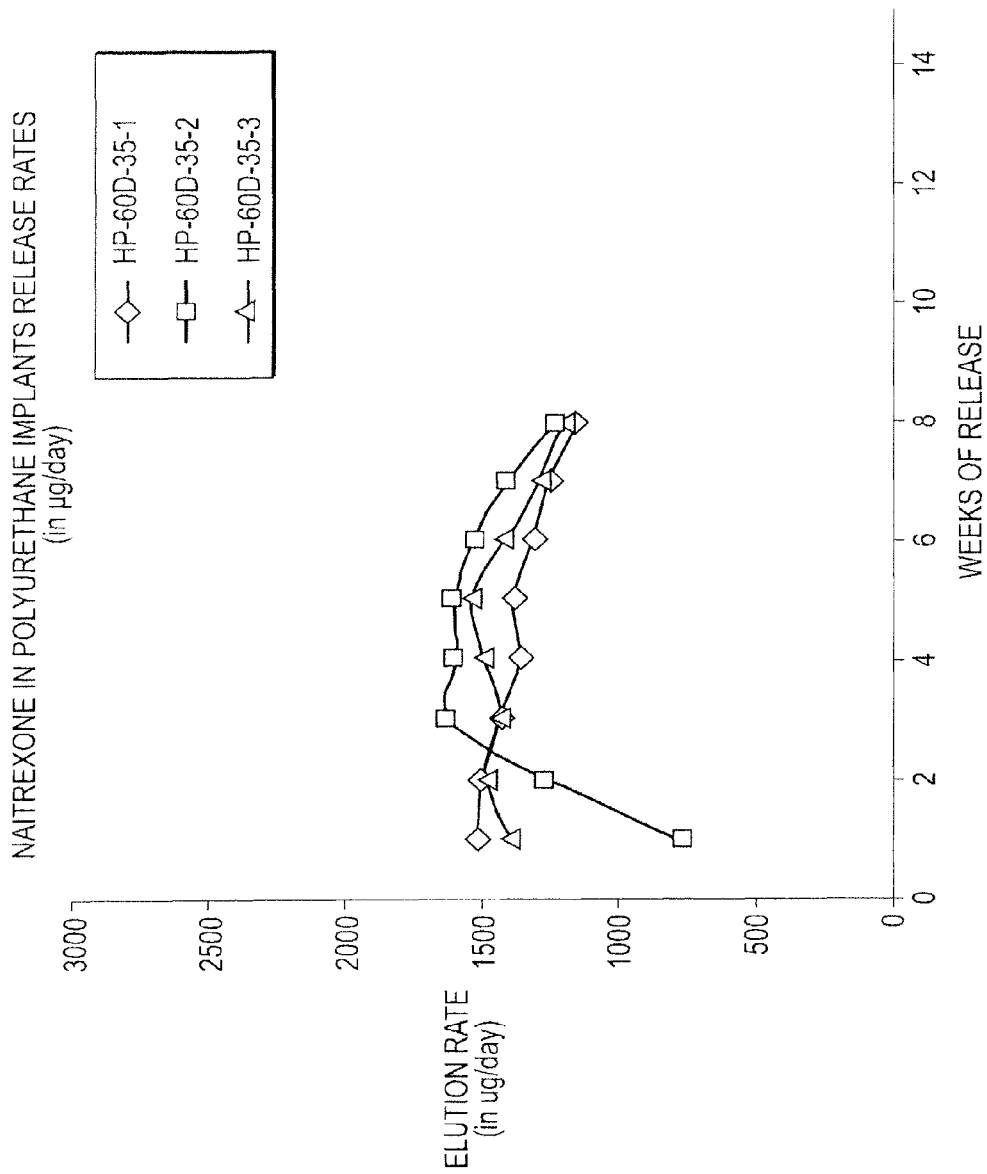
FIG. 5 is a graph of the elution rate of naltrexone from an implant.

HP-60D-35 is extruded to tubes with thickness of 0.30 mm with inside diameter of 1.75 mm. The tubes are then cut into 32 mm in length. One side of the tube is sealed with heat using a heat sealer. The sealing time is less than one minute. Six pellets of naltrexone are loaded into the tubes and both open sides of the tubes are sealed with heat. Each pellet weighs approximately 15.0 mg for a total of 91 mg. The second end open of the tube is sealed with heat in the same way as for the first end. The loaded implant is then conditioned and primed. The conditioning takes place at room temperature in a 0.9% saline solution for one week. Upon completion of the conditioning, the implant undergoes priming. The priming takes place at room temperatures in a 1.8% saline solution for one week. Each implant is tested in vitro in a medium selected to mimic the pH found in the human body. The temperature of the selected medium was kept at approximately 37° C. during the testing. The release rates are shown on FIG. 5 and Table 3.

TABLE 3

Naltrexone Elution Rates

| WEEKS OF RELEASE | HP-60D-35 -1 (μg/day) | HP-60D-35 -2 (μg/day) | HP-60D-35 -3 (μg/day) |
|---|---|---|---|
| 0 | | | |
| 1 | 1529.26 | 767.38 | 1400.95 |
| 2 | 1511.77 | 1280.03 | 1498.86 |
| 3 | 1456.01 | 1635.97 | 1449.49 |
| 4 | 1378.27 | 1607.13 | 1500.42 |
| 5 | 1393.05 | 1614.52 | 1558.37 |
| 6 | 1321.71 | 1550.39 | 1436.03 |
| 7 | 1273.07 | 1424.24 | 1300.73 |
| 8 | 1172.82 | 1246.48 | 1221.57 |

Example 3

Figure 6:
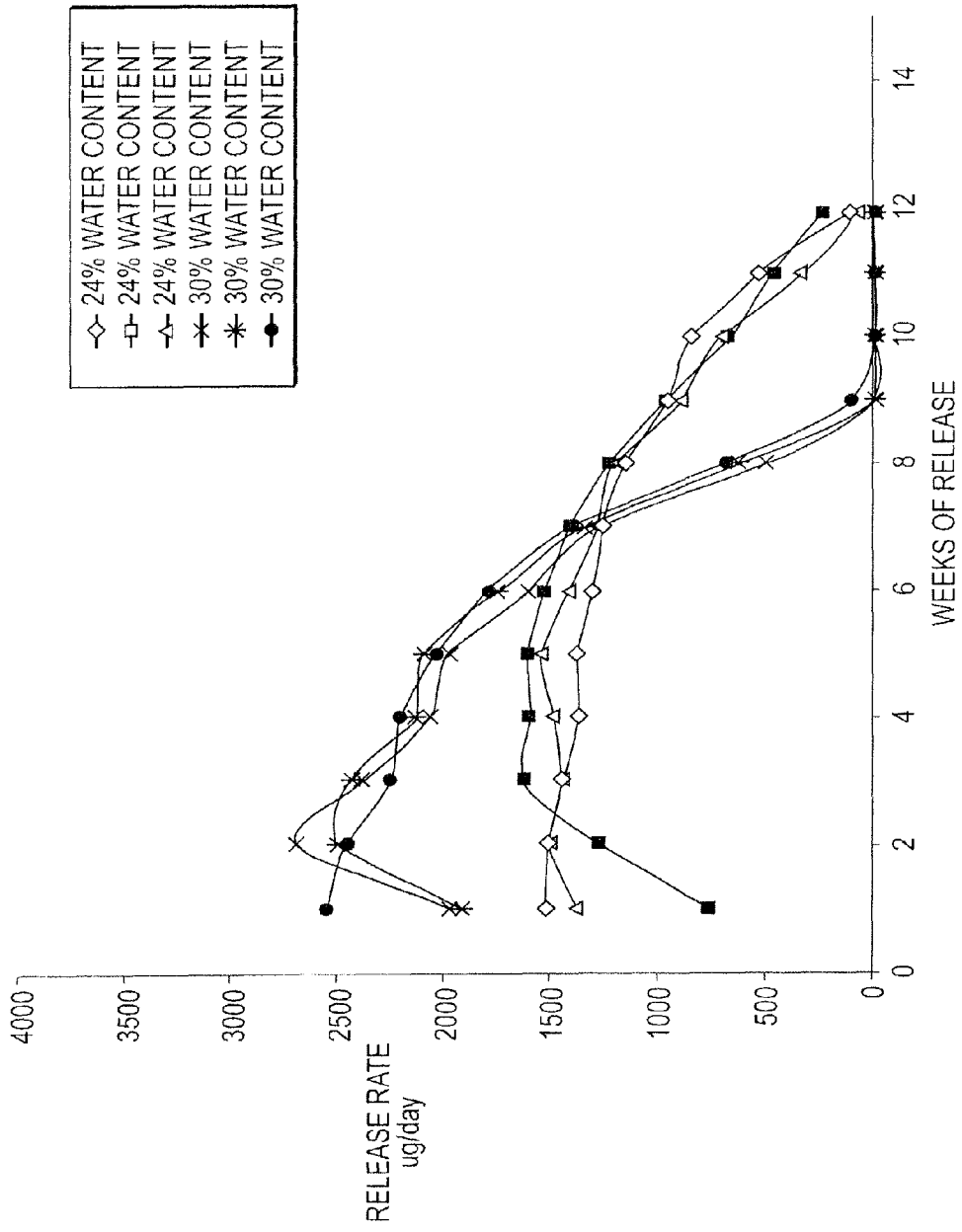
FIG. 6 is a graph of the elution rate of naltrexone from polyurethane implants.

In FIG. 6 there is a comparison of the release rates of naltrexone in vitro using two grades of polymer at two different water contents. Three runs were carried out and analyzed where the polymer of the implant had a water content of 24% and three runs were carried out where the polymer of the implant had a water content of 30%. The release rates were plotted against time. The polymer used for the runs at 24% water content was Tecophilic® HP-60-D35 from Thermedics. The polymer used for the runs at 30% water content was Tecophilic® HP-60-D60 from Thermedics. The data obtained in this example demonstrate the good reproducibility of the implants as prepared according to the present invention.

Example 4

Figure 7:
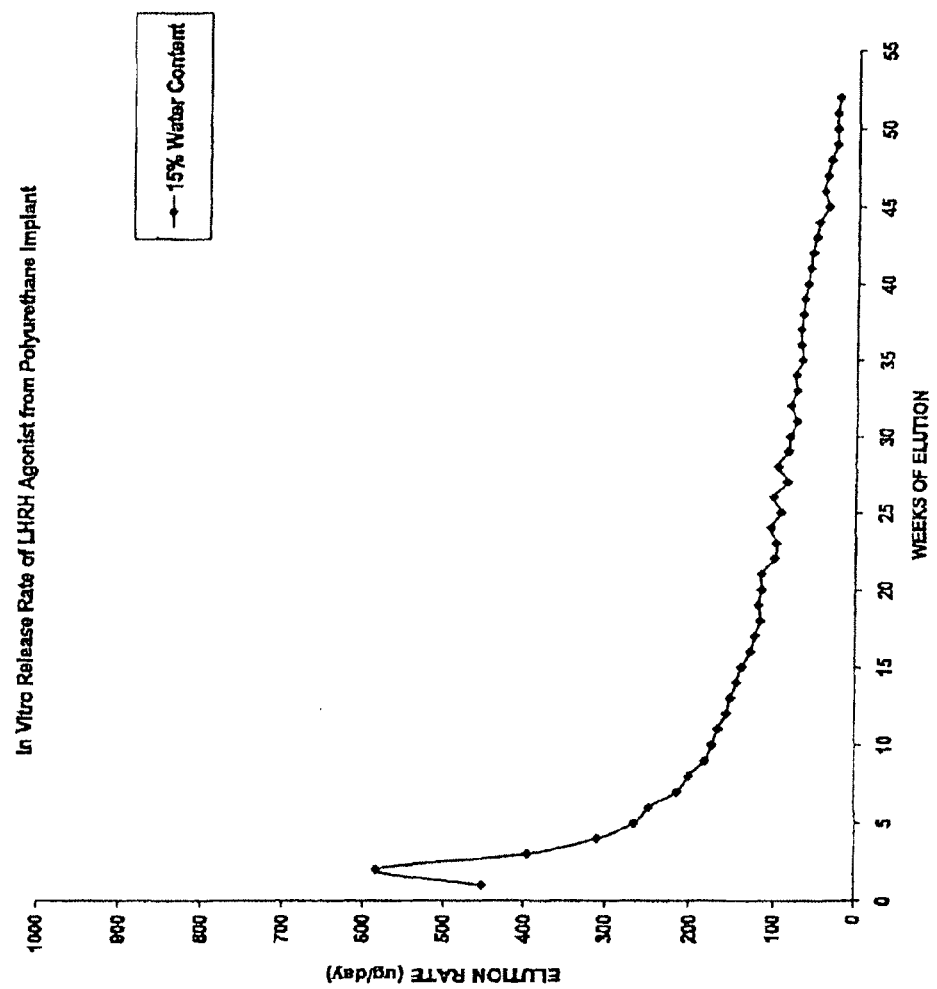
FIG. 7 is a graph of the elution rate of LHRH agonist (histrelin) from a polyurethane implant.

FIG. 7 shows a plot of the release rate of histrelin (LHRH agonist) versus time. The polymer in this example had a water content of 15%. The polymer used was Tecophilic® HP-60-D20 from Thermedics. The data points were taken weekly.

Example 5

Figure 8:
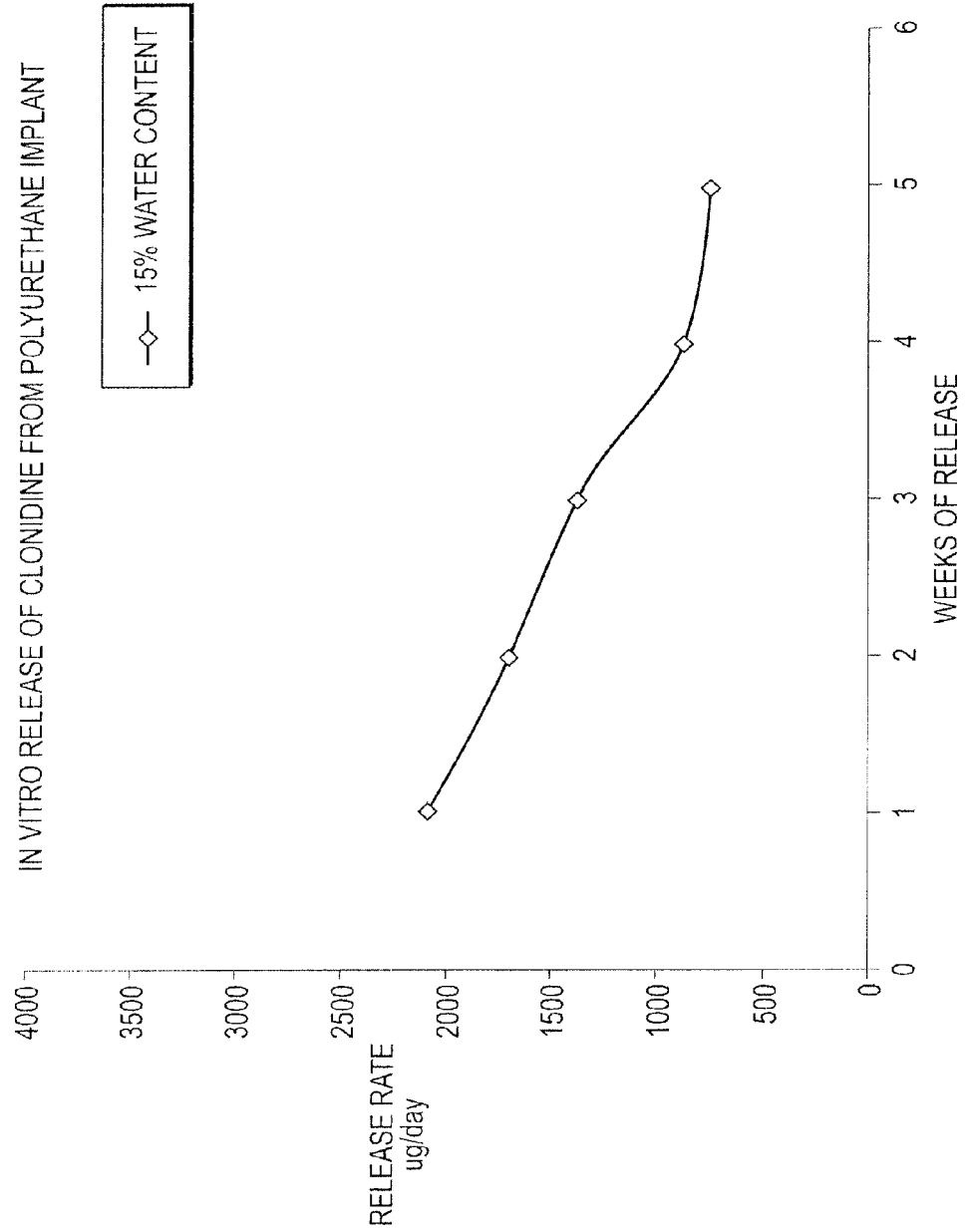
FIG. 8 is a graph of the elution rate of clonidine from a polyurethane implant.

FIG. 8 shows a plot of the release rate of clonidine versus time. The polymer in this example has a water content of 15%. The polymer used was Tecophilic® HP-60-D20 from Thermedics. The data points were taken weekly.

Example 6

Tables 4A-C show release rates of active agents from three different classes of polyurethane compounds (Tecophilic®, Tecoflex® and Carbothane®). The release rates have been normalized to surface area of the implant, thereby adjusting for slight differences in the size of the various implantable devices. The active agents were selected to cover a range of solubilities (as indicated by the varying Log P values; for the purposes of the data provided, a Log P value of greater than about 2.0 is considered to be not readily soluble in aqueous solution) and molecular weights. The polyurethanes were selected to have varying affinities for water soluble active agents and varying flexibility (as indicated by the variation in flex modulus).

For applications of the polyurethanes useful for the devices and methods described herein, the polyurethane exhibits physical properties suitable for the specific active agent to be delivered. Polyurethanes are available or can be prepared, for example, with a range of EWCs or flex moduli (Table 4). Tables 4A-C show normalized release rates for various active ingredients from polyurethane compounds. Tables 4D-F show the non-normalized release rates for the same active ingredients, together with implant composition.

TABLE 4A

| | | Polyurethane Type Tecophilic Polyurethane Grade | | | | |
|---|---|---|---|---|---|---|
| | | HP-60D-60 | HP-60D-35 | HP-60D-20 | HP-60D-10 | HP-60D-05 |
| Active | Relative Water Solubility | 31% EWC | 24% EWC | % EWC/Flex Modulus 15% EWC | 8.7% EWC | 5.5% EWC |
| Octreotide Acetate (M.W. 1019) | Very soluble, Log P = 0.43 | — | 2022 μg/day/cm$^2$ 2% SA 50 mg API | 758 μg/day/cm$^2$ 5% HPC, 2% SA; 50 mg API | 11 μg/day/cm$^2$ 10% HPC, 2% SA, 50 mg API | 0 10% HPC, 2% SA, 50 mg API |
| Histrelin Acetate (M.W. 1323) | Very soluble Log P = (n/a) | 309 μg/day/cm$^2$ 2% SA 50 mg API | 248 μg/day/cm$^2$ 2% SA 50 mg API | 93 μg/day/cm$^2$ 2% SA 50 mg API | — | — |

TABLE 4A-continued

| | | Polyurethane Type Tecophilic Polyurethane Grade | | | | |
|---|---|---|---|---|---|---|
| | | HP-60D-60 | HP-60D-35 | HP-60D-20 | HP-60D-10 | HP-60D-05 |
| | Relative Water | | | % EWC/Flex Modulus | | |
| Active | Solubility | 31% EWC | 24% EWC | 15% EWC | 8.7% EWC | 5.5% EWC |
| Selegiline HCL (M.W. 224) | Freely soluble Log P = (n/a) | — | — | 294 µg/day/cm$^2$ 2% SA 66.8 mg API | — | — |
| Dexamethasone (M.W. 392) | Log P = 1.93 | — | — | 85 µg/day/cm$^2$ 10% CC, 2% SA, 47.5 mg API | — | — |
| Naltrexone Base (M.W. 285) | Log P = 2.07 | 883 µg/day/cm$^2$ 10% CC, 2% SA + PEG 400, 79.2 mg API | 704 µg/day/cm$^2$ 2% SA 91.3 mg API | 263 µg/day/cm$^2$ 10% CC, 2% SA, 193.6 mg API | 127 µg/day/cm$^2$ 10% CC, 2% SA + PEG 400, 197.1 mg API | 12.7 µg/day/cm$^2$ 10% CC, 2% SA, 144.6 mg API |
| Metolazone (M.W. 366) | Log P = 2.50 | — | — | 50 µg/day/cm$^2$ 10% CC, 2% SA, 82.7 mg API | — | — |
| Clonidine Base (M.W. 230) | Log P = 2.56 | — | — | 1011 µg/day/cm$^2$ 2% SA ~50 mg API | — | — |
| Risperidone (M.W. 410) | Log P = 3.28 | — | — | 149 µg/day/cm$^2$ 10% CC, 2% SA, 28.5 mg API | — | — |

TABLE 4B

| | | Polyurethane Type Tecoflex Polyurethane Grade | | |
|---|---|---|---|---|
| | Relative Water | EG-85A | EG 100A | EG-65D |
| | | | % EWC/Flex Modulus | |
| Active | Solubility | F.M.: 2,300 | F.M.: 10,000 | F.M.: 37,000 |
| Octreotide Acetate (M.W. 1019) | Very soluble, Log P = 0.43 | 16 µg/day/cm$^2$ 10% HPC, 2% SA, 50 mg API | — | — |
| Histrelin Acetate (M.W. 1323) | Very soluble Log P = (n/a) | — | 0.3 µg/day/cm$^2$ 2% SA 50 mg API | — |
| Selegiline HCL (M.W. 224) | Freely soluble Log P = (n/a) | 1518 µg/day/cm$^2$ 2% SA 67.2 mg API | 7.2 µg/day/cm$^2$ 2% SA 63.5 mg API | 4.1 µg/day/cm$^2$ 2% SA 63.1 mg API |
| Dexa-methasone (M.W. 392) | Log P = 1.93 | 40 µg/day/cm$^2$ 10% CC, 2% SA, 47.3 mg API | 2.6 µg/day/cm$^2$ 10% CC, 2% SA, 54.5 mg API | 0.5 µg/day/cm$^2$ 10% CC, 2% SA, 53.1 mg API |
| Naltrexone Base (M.W. 285) | Log P = 2.07 | — | 23 µg/day/cm$^2$ 10% CC, 2% SA, 75.5 mg API | — |
| Metolazone (M.W. 366) | Log P = 2.50 | 32 µg/day/cm$^2$ 10% CC, 2% SA, 82.7 mg API | 2.3 µg/day/cm$^2$ 10% CC, 2% SA, 82.0 mg API | — |
| Clonidine Base (M.W. 230) | Log P = 2.56 | 1053 µg/day/cm$^2$ 20% CC, 2% SA, 80.3 mg API | 88 µg/day/cm$^2$ 20% CC, 2% SA, 65.7 mg API | 25 µg/day/cm$^2$ 20% CC, 2% SA, 66.3 mg API |
| Risperidone (M.W. 410) | Log P = 3.28 | 146 µg/day/cm$^2$ 10% CC, 2% SA, 27.9 mg API | 7.6 µg/day/cm$^2$ 10% CC, 2% SA, 29.8 mg API | 1.9 µg/day/cm$^2$ 10% CC, 2% SA, 29.7 mg API |

TABLE 4C

| | | Polyurethane Type Carbothane | |
|---|---|---|---|
| | | Polyurethane Grade | |
| | Relative Water | PC-3575A | PC-3595A |
| | | % EWC/Flex Modulus | |
| Active | Solubility | F.M.: 620 | F.M.: 4,500 |
| Octreotide Acetate (M.W. 1019) | Very soluble, Log P = 0.43 | — | — |
| Histrelin Acetate (M.W. 1323) | Very soluble Log P = (n/a) | — | 0.2 µg/day/cm² 2% SA 50 mg API |
| Selegiline HCL (M.W. 224) | Freely soluble Log P = (n/a) | 36 µg/day/cm² 2% SA 65.3 mg API | 15 µg/day/cm² 2% SA 66.8 mg API |
| Dexamethasone (M.W. 392) | Log P = 1.93 | 6.2 µg/day/cm² 10% CC, 2% SA, 47.1 mg API | 2.3 µg/day/cm² 10% CC, 2% SA, 53.2 mg API |
| Naltrexone Base (M.W. 285) | Log P = 2.07 | — | 5.5 µg/day/cm² 10% CC, 2% SA, 189.2 mg API |
| Metolazone (M.W. 366) | Log P = 2.50 | 8.4 µg/day/cm² 10% CC, 2% SA, 82.7 mg API | 2.6 µg/day/cm² 10% CC, 2% SA, 81.6 mg API |
| Clonidine Base (M.W. 230) | Log P = 2.56 | 202 µg/day/cm² 20% CC, 2% SA, 66.5 mg API | 136 µg/day/cm² 20% CC, 2% SA, 64.6 mg API |
| Risperidone (M.W. 410) | Log P = 3.28 | 40 µg/day/cm² 10% CC, 2% SA, 27.8 mg API | 11 µg/day/cm² 10% CC, 2% SA, 29.7 mg API |

TABLE 4D

| | | Polyurethane Tecophilic Grade | | | | |
|---|---|---|---|---|---|---|
| | Relative Water | HP-60D-60 | HP-60D-35 | HP-60D-20 | HP-60D-10 | HP-60D-05 |
| | | % EWC | | | | |
| Active | Solubility | 31% EWC | 24% EWC | 15% EWC | 8.7% EWC | 5.5% EWC |
| Octreotide Acetate (M.W. 1019) | Very soluble, Log P = 0.43 | — | 4000 µg/day ID: 1.80 mm Wall: 0.30 mm L: 30 mm 1.978 cm² | 1500 µg/day ID: 1.80 mm Wall: 0.30 mm L: 30 mm 1.978 cm² | 25 µg/day ID: 1.83 mm Wall: 0.30 mm L: 34 mm 2.274 cm² | 0 |
| Histrelin Acetate (M.W. 1323) | Very soluble Log P = (n/a) | 500 µg/day ID: 1.80 mm Wall: 0.30 mm L: 24.5 mm 1.616 cm² | 400 µg/day ID: 1.80 mm Wall: 0.30 mm L: 24.5 mm 1.616 cm² | 150 µg/day ID: 1.80 mm Wall: 0.30 mm L: 24.5 mm 1.616 cm² | — | — |
| Selegiline HCL (M.W. 224) | Freely soluble Log P = (n/a) | — | — | 600 µg/day ID 1.80 mm Wall: 0.3 mm L: 30.9 mm 2.038 cm² | — | — |
| Dexamethasone (M.W. 392) | Log P = 1.93 | — | — | 170 µg/day ID: 1.80 mm Wall: 0.30 mm L: 30.24 mm 1.994 cm² | — | — |
| Naltrexone Base (M.W. 285) | Log P = 2.07 | 2200 µg/day ID: 1.80 mm Wall: 0.30 mm L: 37.8 mm 2.492 cm² | 1500 µg/day ID: 2.87 mm Wall: 0.30 mm L: 32.3 mm 2.130 cm² | 1000 µg/day ID: 1.80 mm Wall: 0.38 mm L: 37.2 mm 3.796 cm² | 500 µg/day ID: 3.05 mm Wall: 0.30 mm L: 37.3 mm 3.924 cm² | 50 µg/day ID: 3.05 mm Wall: 0.30 mm L: 37.4 mm 3.934 cm² |
| Metolazone (M.W. 366) | Log P = 2.50 | — | — | 124 µg/day ID: 1.80 mm Wall: 0.30 mm L: 37.4 mm 2.466 cm² | — | — |
| Clonidine Base (M.W. 230) | Log P = 2.56 | — | — | 2000 µg/day ID: 1.80 mm Wall: 0.30 mm L: 30.0 mm 1.978 cm² | — | — |
| Risperidone (M.W. 410) | Log P = 3.28 | — | — | 150 µg/day ID: 1.80 mm Wall: 0.30 mm L: 15.24 mm 1.005 cm² | — | — |

TABLE 4E

| Active | Relative Water Solubility | Polyurethane Type Tecoflex Polyurethane Grade | | |
|---|---|---|---|---|
| | | EG-85A Flex Modulus F.M.: 2,300 | EG 100A Flex Modulus F.M.: 10,000 | EG-65D Flex Modulus F.M.: 37,000 |
| Octreotide Acetate (M.W. 1019) | Very soluble, Log P = 0.43 | 30 µg/day ID: 1.85 mm Wall: 0.20 mm L: 30 mm 1.931 cm² | — | — |
| Histrelin Acetate (M.W. 1323) | Very soluble Log P = (n/a) | — | 0.5 µg/day ID: 1.85 mm Wall: 0.20 mm L; 25.56 mm 1.645 cm² | — |
| Selegiline HCL (M.W. 224) | Freely soluble Log P = (n/a) | 3000 µg/day ID: 1.85 mm Wall: 0.20 mm L: 30.7 mm 1.976 cm² | 14 µg/day ID: 1.85 mm Wall: 0.2 mm L: 30.2 mm 1.944 cm² | 8 µg/day ID: 1.85 mm Wall: 0.20 mm L: 30.4 mm 1.957 cm² |
| Dexa-methasone (M.W. 392) | Log P = 1.93 | 80 µg/day ID: 1.85 mm Wall: 0.20 mm L: 30.9 mm 1.989 cm² | 5 µg/day ID: 1.85 mm Wall: 0.20 mm L: 30.0 mm 1.931 cm² | 1.0 µg/day ID: 1.85 mm Wall: 0.20 mm L: 30.7 mm 1.976 cm² |
| Naltrexone Base (M.W. 285) | Log P = 2.07 | — | 55 µg/day ID: 1.85 mm Wall: 0.20 mm L: 37.49 mm 2.413 cm² | — |
| Metolazone (M.W. 366) | Log P = 2.50 | 77 µg/day ID: 1.85 mm Wall: 0.20 mm L: 37.7 mm 2.427 cm² | 5.5 µg/day ID: 1.85 mm Wall: 0.20 mm L: 37.15 mm 2.391 cm² | — |
| Clonidine Base (M.W. 230) | Log P = 2.56 | 2000 µg/day ID: 1.85 mm Wall: 0.20 mm L: 29.5 mm 1.899 cm² | 175 µg/day ID: 1.85 mm Wall: 0.20 mm L: 30.8 mm 1.983 cm² | 50 µg/day ID: 1.85 mm Wall: 0.20 mm L: 30.8 mm 1.983 cm² |
| Risperidone (M.W. 410) | Log P = 3.28 | 150 µg/day ID: 1.85 mm Wall: 0.20 mm L: 16.0 mm 1.030 cm² | 8 µg/day ID: 1.85 mm Wall: 0.20 mm L: 16.4 mm 1.056 cm² | 2 µg/day ID: 1.85 mm Wall: 0.20 mm L: 16.2 mm 1.043 cm² |

TABLE 4F

| Active | Relative Water Solubility | Polyurethane Type Carbothane Polyurethane Grade | |
|---|---|---|---|
| | | PC-3575A Flex Modulus F.M.: 620 | PC-3595A Flex Modulus F.M.: 4,500 |
| Octreotide Acetate (M.W. 1019) | Very soluble, Log P = 0.43 | — | — |
| Histrelin Acetate (M.W. 1323) | Very soluble Log P = (n/a) | — | 0.4 µg/day ID: 1.85 mm Wall: 0.20 mm L: 25.25 mm 1.625 cm² |
| Selegiline HCL (M.W. 224) | Freely soluble Log P = (n/a) | 70 µg/day ID: 1.85 mm Wall: 0.20 mm L: 29.9 mm 1.925 cm² | 30 µg/day ID: 1.85 mm Wall: 0.20 mm L: 30.6 mm 1.970 cm² |
| Dexa-methasone (M.W. 392) | Log P = 1.93 | 12 µg/day ID: 1.85 mm Wall: 0.20 mm L: 30.0 mm 1.931 cm² | 4.5 µg/day ID: 1.85 mm Wall: 0.20 mm L: 30.7 mm 1.976 cm² |
| Naltrexone Base (M.W. 285) | Log P = 2.07 | — | 25 µg/day ID: 3.63 mm Wall: 0.18 mm L: 38.19 mm 4.569 cm² |
| Metolazone (M.W. 366) | Log P = 2.50 | 20 µg/day ID: 1.85 mm Wall: 0.20 mm L: 37.0 mm 2.382 cm² | 6.1 µg/day ID: 1.85 mm Wall: 0.20 mm L: 37.02 mm 2.383 cm² |

TABLE 4F-continued

|  | Relative Water Solubility | Polyurethane Type Carbothane Polyurethane Grade | |
|---|---|---|---|
|  |  | PC-3575A | PC-3595A |
|  |  | Flex Modulus | |
| Active |  | F.M.: 620 | F.M.: 4,500 |
| Clonidine Base (M.W. 230) | Log P = 2.56 | 400 µg/day ID: 1.85 mm Wall: 0.20 mm L: 30.8 mm 1.983 cm² | 270 µg/day ID: 1.85 mm Wall: 0.20 mm L: 30.8 mm 1.983 cm² |
| Risperidone (M.W. 410) | Log P = 3.28 | 40 µg/day ID: 1.85 mm Wall: 0.20 mm L: 15.6 mm 1.004 cm² | 11 µg/day ID: 1.85 mm Wall: 0.20 mm L: 16.2 mm 1.043 cm² |

The solubility of an active agent in an aqueous environment can be measured and predicted based on its partition coefficient (defined as the ratio of concentration of compound in aqueous phase to the concentration in an immiscible solvent). The partition coefficient (P) is a measure of how well a substance partitions between a lipid (oil) and water. The measure of solubility based on P is often given as Log P. In general, solubility is determined by Log P and melting point (which is affected by the size and structure of the compounds). Typically, the lower the Log P value, the more soluble the compound is in water. It is possible, however, to have compounds with high Log P values that are still soluble on account of, for example, their low melting point. It is similarly possible to have a low Log P compound with a high melting point, which is very insoluble.

The flex modulus for a given polyurethane is the ratio of stress to strain. It is a measure of the "stiffness" of a compound. This stiffness is typically expressed in Pascals (Pa) or as pounds per square inch (psi).

The elution rate of an active agent from a polyurethane compound can vary on a variety of factors including, for example, the relative hydrophobicity/hydrophilicity of the polyurethane (as indicated, for example, by log P), the relative "stiffness" of the polyurethane (as indicated, for example, by the flex modulus), and/or the molecular weight of the active agent to be released.

Example 7

Elution of Risperidone from Polyurethane Implantable Devices

FIGS. 9-14 are graphs showing elution profiles of risperidone from various implantable devices over varying periods of time.

Figure 9A:
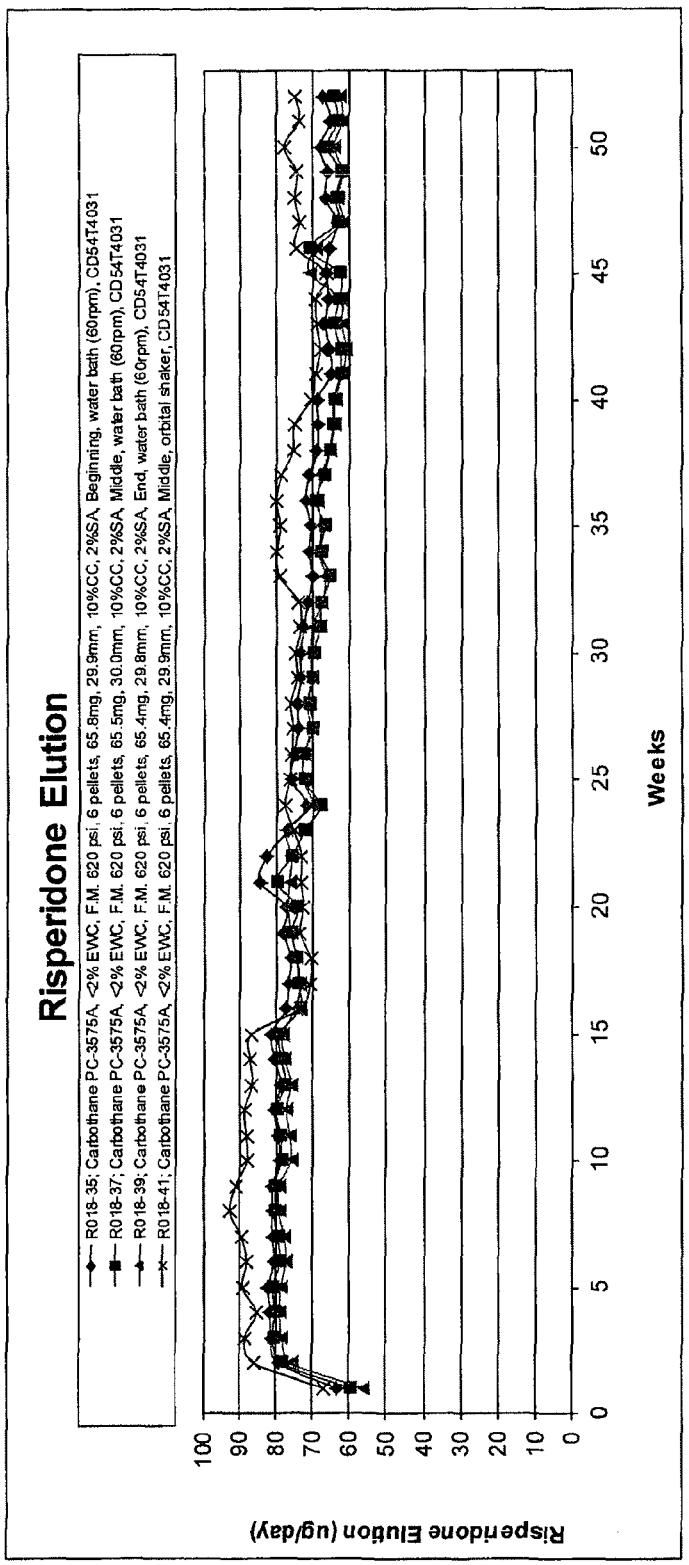
FIGS. 9A and 9B are graphs showing elution from Carbothane® PC-3575A.
Figure 9B:
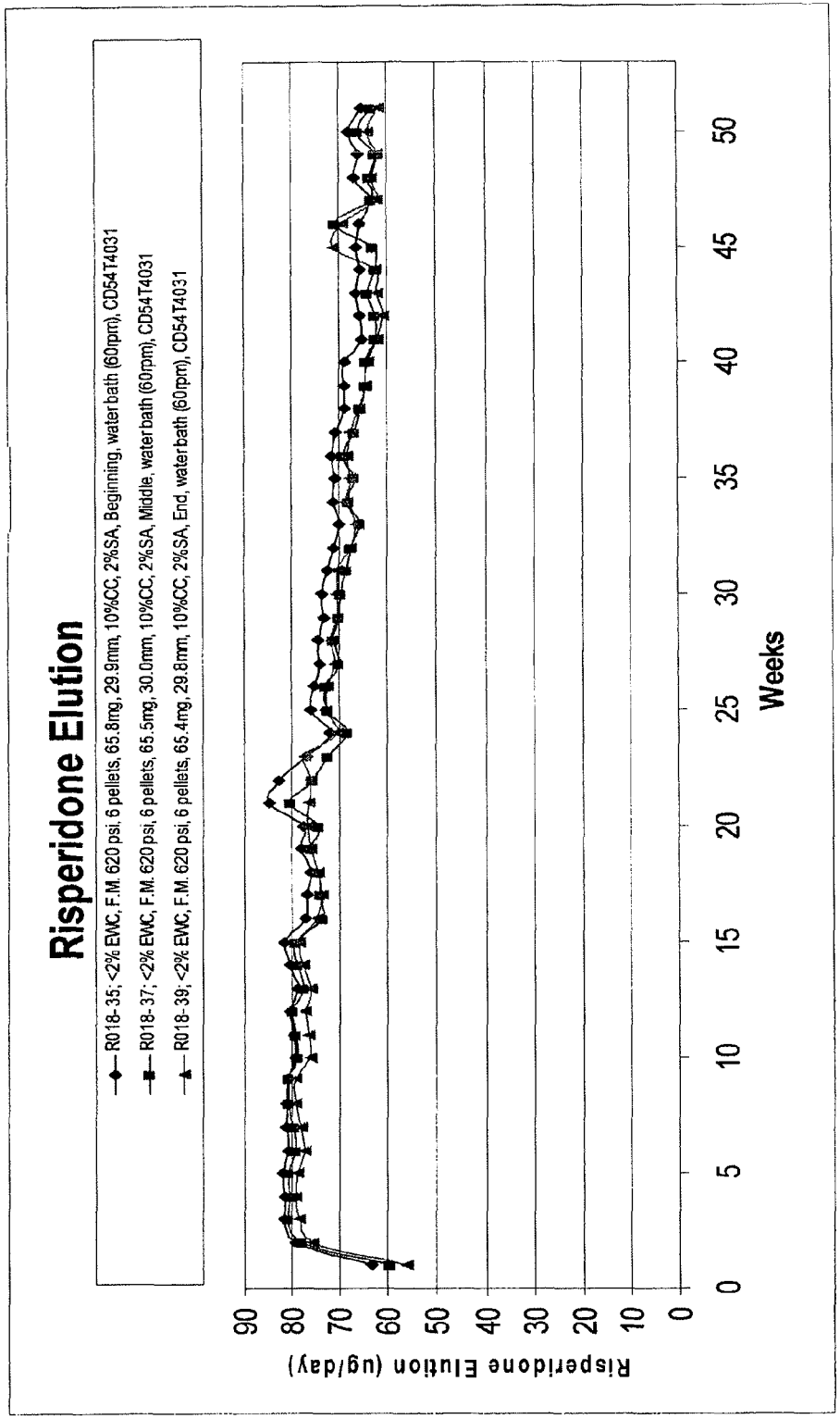

Release rates were obtained for risperidone from Carbothane® PC-3575A polyurethane implants (F.M. 620 psi) prepared from tubing sections representing the beginning, middle and end of a coil of tubing as part of an assessment of the uniformity of the material within a particular lot (FIG. 9). Samples were evaluated weekly for one year. All implants were of equivalent geometry and drug load.

Figure 10:
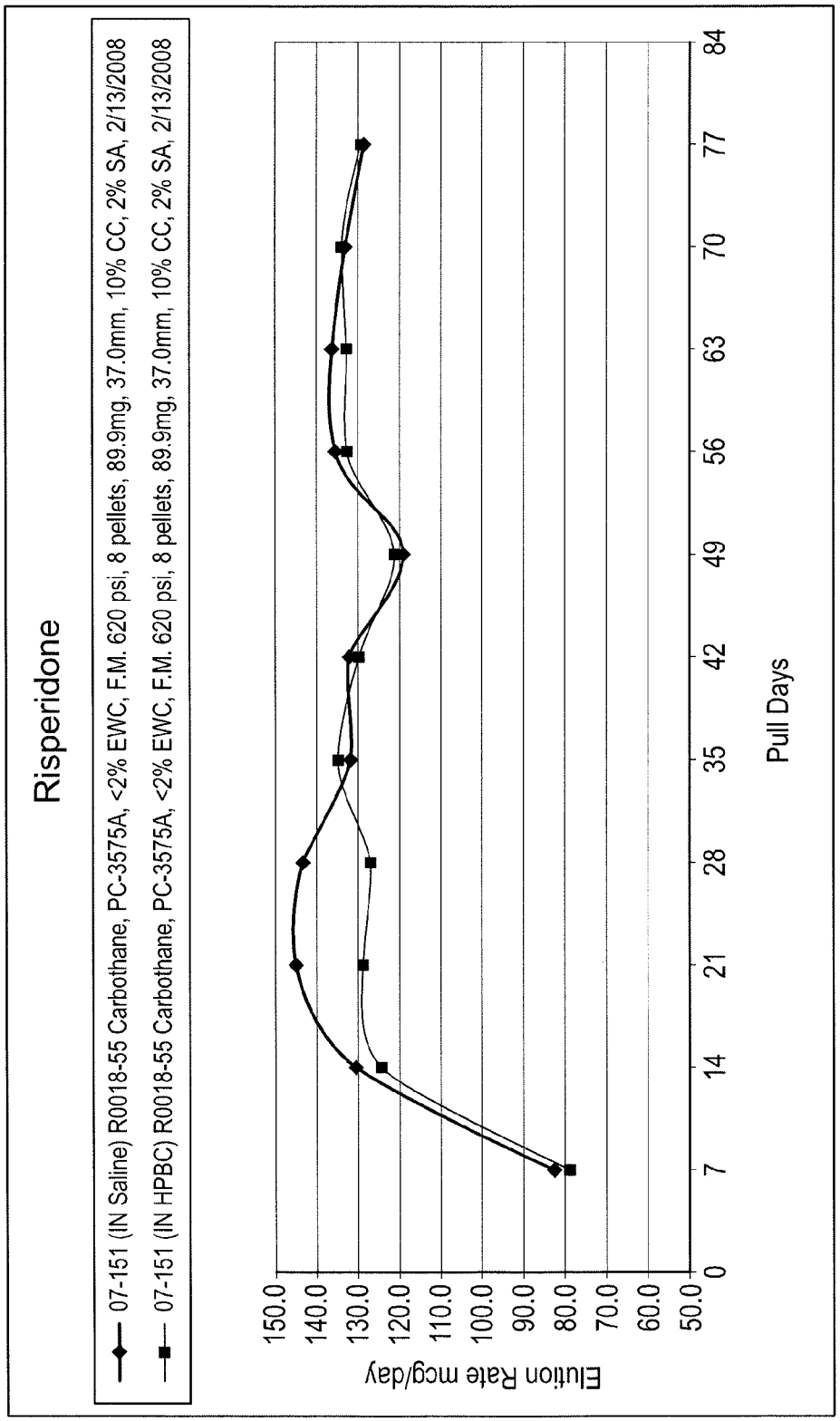
FIG. 10 is a graph of the release rate of risperidone from Carbothane® PC-3575A polyurethane implants (Flex Modulus 620 psi) as part of an assessment of the effect using saline versus aqueous hydroxypropyl betacellulose solution (15% in phosphate buffered saline) as the elution media. Samples were evaluated weekly for 11 weeks. All implants were of equivalent geometry and drug load.

Release rates were obtained for risperidone from Carbothane® PC-3575A polyurethane implants (F.M. 620 psi) as part of an assessment of the effect using saline versus aqueous hydroxypropyl betacellulose solution (15% in phosphate buffered saline) as the elution media (FIG. 10). Samples were evaluated weekly for 11 weeks. All implants were of equivalent geometry and drug load.

Figure 11A:
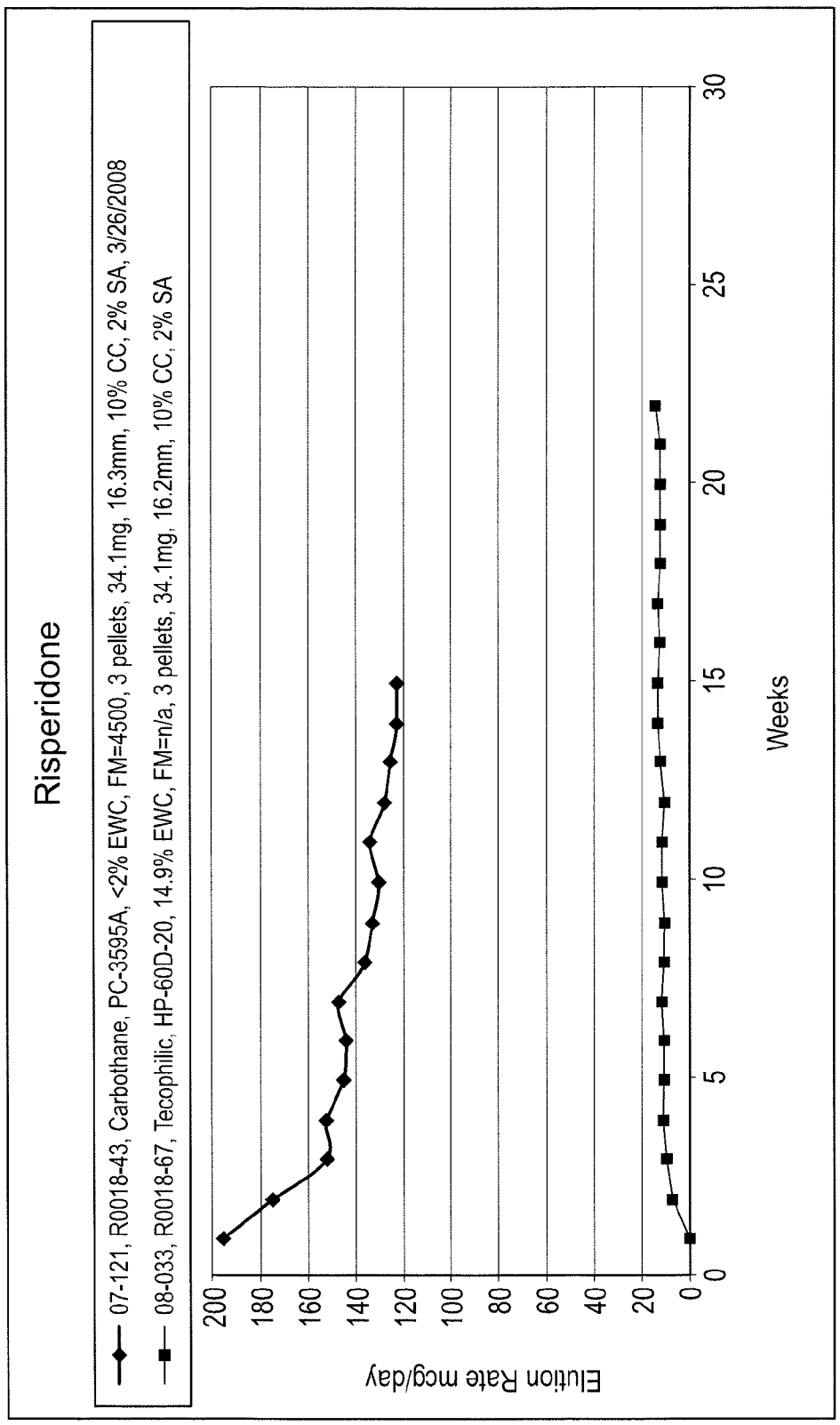
FIGS. 11A and 11B are graphs comparing the release rates of risperidone from Carbothane® PC-3595A polyurethane implants (Flex modulus 4500 psi) to Tecophilic® HP-60D-20 polyurethane implants (EWC, 14.9%) as part of the evaluation of the release of the active from either hydrophilic and hydrophobic polyurethane materials. Samples were evaluated weekly for 22 weeks for the Carbothane® implant. Samples were evaluated weekly for 15 weeks for the Tecophilic® implant. All implants were of equivalent geometry and drug load.
Figure 11B:
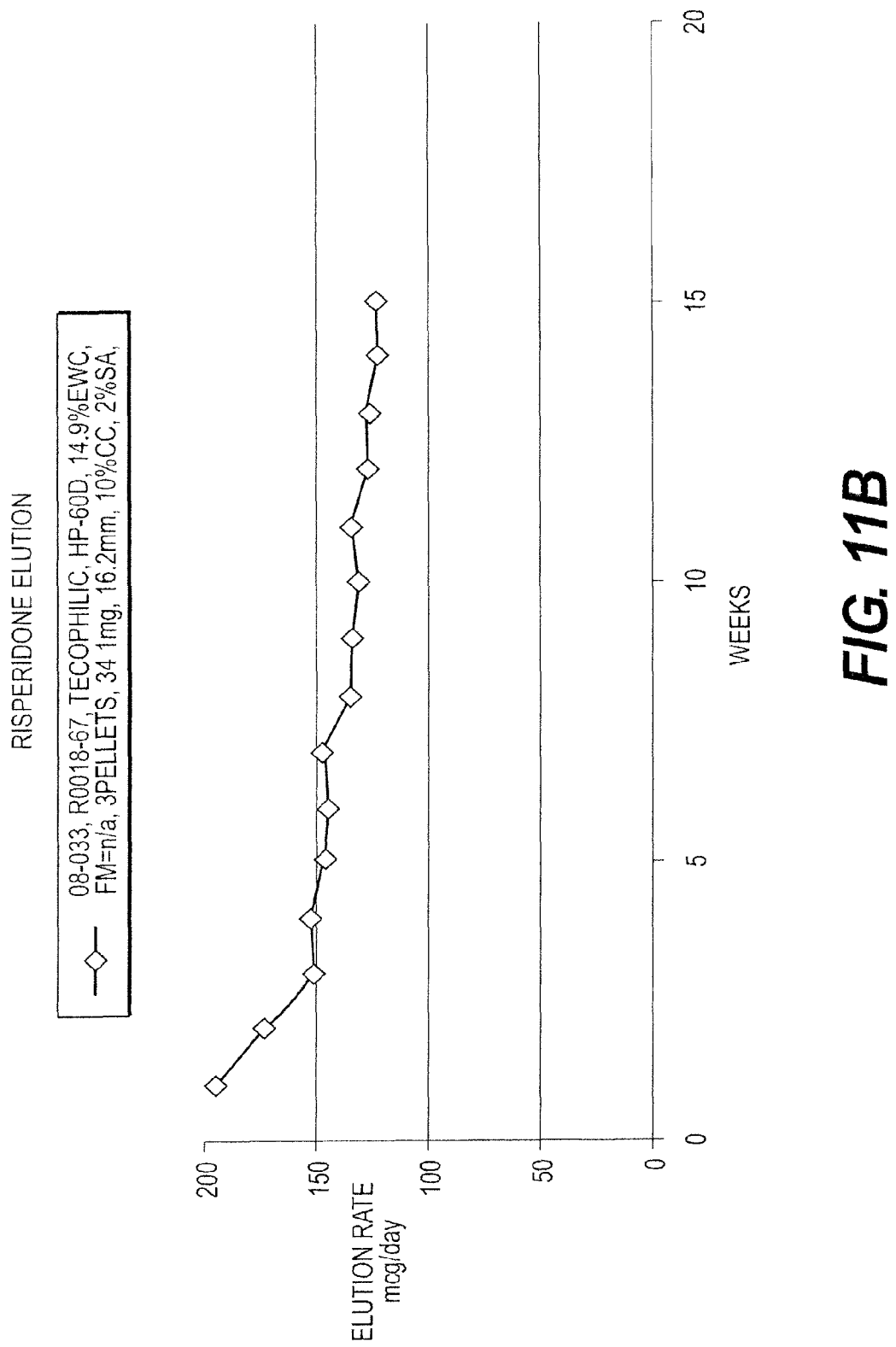

Release rates were compared for risperidone from Carbothane® PC-3595A polyurethane implants (F.M. 4500 psi) and Tecophilic® HP-60D-20 polyurethane implants (EWC 14.9%) as part of the evaluation of the release of the active from either hydrophilic and hydrophobic polyurethane materials (FIGS. 11A and 11B). Samples were evaluated weekly for 22 weeks for the Carbothane® implant. Samples were evaluated weekly for 15 weeks for the Tecophilic® implant. All implants were of equivalent geometry and drug load.

Figure 12:
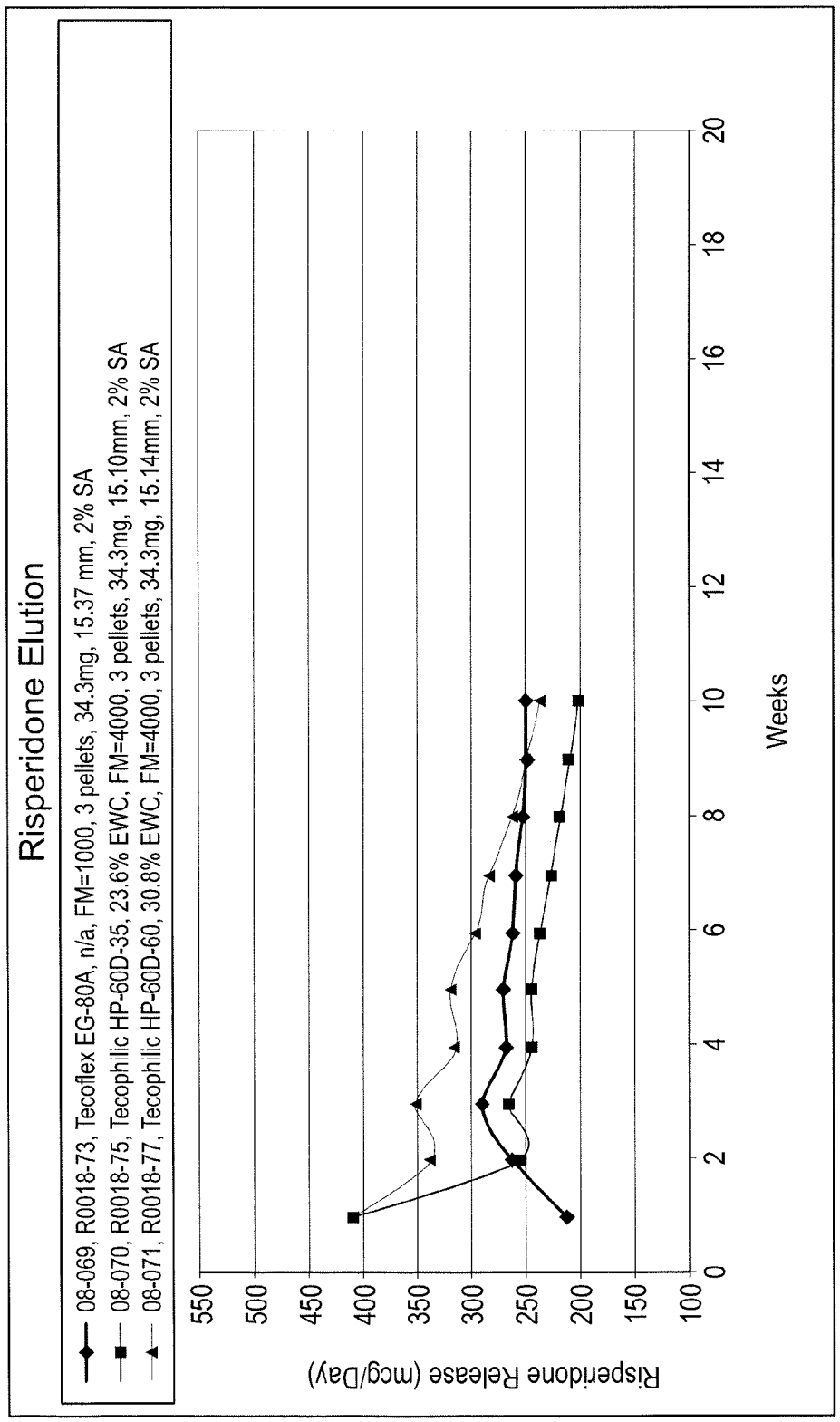
FIG. 12 is a graph comparing the release rates of risperidone from Tecoflex® EG-80A polyurethane implants (Flex Modulus 1000 psi) and two grades of Tecophilic® polyurethane implants, HP-60D-35 and HP-60D-60 (EWC, 23.6% and 30.8%, respectively). All were sampled weekly for 10 weeks. All implants were of equivalent geometry and drug load.
Figure 13:
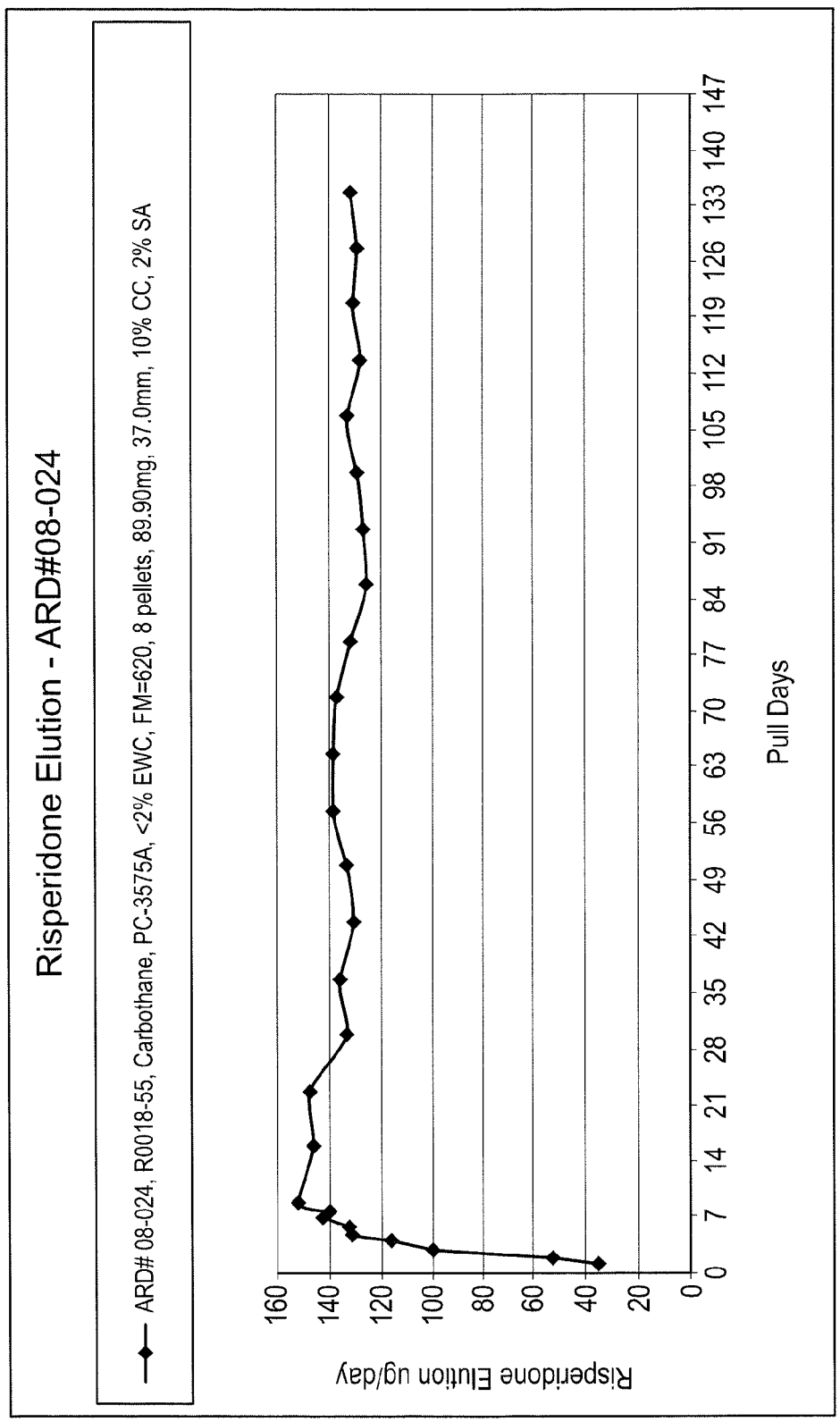
FIG. 13 is a graph of the release rate of risperidone from Carbothane® PC-3575A polyurethane implants (Flex Modulus 620 psi) that served as in vitro controls for implants used in the beagle dog study described in Example 8. The in vitro elution study of these implants was initiated on the date of implantation of the subject implants as part of an assessment of in vivo-in vitro correlation.

Release rates were compared for risperidone from Tecoflex® EG-80A polyurethane implants (F.M. 1000 psi) and two grades of Tecophilic® polyurethane implants, HP-60D-35 and HP-60D-60 (EWC, 23.6% and 30.8%, respectively) (FIG. 12). All were sampled weekly for 10 weeks. All implants were of equivalent geometry and drug load.

Release rates were obtained for risperidone from Carbothane® PC-3575A polyurethane implants (F.M. 620 psi) that served as in vitro controls for implants used in the beagle dog study described in Example 8. The in vitro elution study of these implants was initiated on the date of implantation of the subject implants as part of an assessment of in vivo-in vitro correlation.

Example 8

Evaluation of Polyurethane Subcutaneous Implant Devices Containing Risperidone in Beagle Dogs The purposes of this study are to determine the blood levels of risperidone from one or two implants and the duration of time the implants will release drug. Polyurethane-based implantable devices comprising a pellet comprising risperidone were implanted into beagles to determine release rates of risperidone in vivo. The results of the sample analysis are summarized in Table 5 and FIG. 14. Risperidone is still present at a high level in the dog plasma at the end of the third month. The study was conducted in accordance with WCFP's standard operating procedures (SOPs), the protocol, and any protocol amendments. All procedure were conducted in accordance with the Guide for the Care and Use of Laboratory Animals (National Research Center, National Academy Press, Washington, D.C., 1996), and approved by the Institutional Animal Care and Use Committee in WCFP.

The implants initially contained about 80 mg of risperidone and are designed to deliver approximately 130 mcg/day for 3 months. The test article was stored at between 2-8° C. before use.

The animals were as follows:
Species: Canine
Strain: Beagle dog
Source: Guangzhou Pharm. Industril Research Institute,
Certification No: SCXK(YUE)2003-0007
Age at Initiation of Treatment: 6~9 months
Weight: 8~10 kg
Number and Sex: 6 males Prior to study initiation, animals were assigned a pretreatment identification number. All animals were weighed before administration once weekly, and received cage-side observations daily by qualified veterinarian during acclimation period. All animals were given a clinical examination prior to selection for study. Animals with any evidence of disease or physical abnormalities were not selected for study. The blood sampling was taken as Baseline at the 3rd and 2nd day before implant. Animals were then randomized into to 2 groups, with the dosing schedule provided as follows:

| Group | Dose Route | No. of Animals Male | Dose rate (mcg/day) | Total Dose (mg) |
|---|---|---|---|---|
| 1 | Subcutaneous implant | 3 | 130 | 23 (single implant) |
| 2 | Subcutaneous implant | 3 | 260 | 46 (double implants) |

Each animal was anesthetized by general anesthesia via pentobarbital sodium at the dose of 30 mg/kg for device implantation. The drug was released at a steady rate for several months. Half the animals received one implant (group 1) and the others received two implants (group 2). A 5 cm² area of the shoulder was shaved and 2 mL of marcaine infused under the skin to numb the area. A small incision was made on the shoulder and the device was slid under the skin. The small incision was closed and the animal was allowed to recover and return to his run. Over the next five to seven days, the implantation site was be monitored for signs of infection or reaction. The skin staples were removed when the skin has healed sufficiently. At the end of three months, the devices were removed, just as they would clinically.

Animals were fasted at least four hours prior to blood sampling. Since blood sampling was done in the morning, food was withheld overnight. Blood samples were drawn using a 20G needle and collected directly into the 5 mL tubes containing sodium heparin and maintained chilled until centrifugation. Samples were then centrifuged at 5000 RPM for 5 minutes at 4° C. The separated plasma was then be transferred into two 3 mL cryo tubes. The samples were labeled with the actual date the sample was taken, the corresponding study day, the dog identification and the duplicate sample designator (either A or B). Samples were kept at −20° C. until ready for analysis.

On two consecutive days, prior to implantation of the delivery device, baseline blood samples were taken. In addition, daily blood samples were taken during the first week and weekly blood samples were taken for the three months following implantation. Two 5 mL blood samples were drawn at each time from each dog. Blood samples were drawn from the cephalic veins primarily; with the saphenous or jugular used as a backup. For both the single and double implant groups, blood samples were drawn at appropriate times as outlined in Table 5 below. Analysis required at least 2 mL of plasma, which required no less than 10 mL of blood drawn for each sample. Analysis of plasma concentrations of risperidone was performed using an LC/MS assay developed for this compound. A single assay was be run for each sample. Samples were collected, held at the appropriate condition and analyzed in batches.

TABLE 5

Concentration of Risperidone in Dog Plasma

| Date | Week | Day | Group 1 (single implant) | | | Group 2 (double implants) | | | Group 1 | | Group 2 | |
|---|---|---|---|---|---|---|---|---|---|---|---|---|
| | | | 1M01 | 1M02 | 1M03 | 2M01 | 2M02 | 2M03 | Mean | S.D. | Mean | S.D. |
| | | −3 | — | — | — | — | — | — | | | | |
| | | −2 | — | — | — | — | — | — | | | | |
| 1.29 | 1 | 1 | BLQ | BLQ | 0.26 | BLQ | 0.54 | BLQ | 0.26 | / | 0.54 | / |
| 1.30 | 1 | 2 | 0.77 | BLQ | 0.24 | 0.53 | 1.86 | 0.46 | 0.51 | 0.37 | 0.95 | 0.79 |
| 1.31 | 1 | 3 | 1.16 | 0.78 | 0.37 | 1.15 | 2.70 | 0.92 | 0.77 | 0.40 | 1.59 | 0.97 |
| 2.01 | 1 | 4 | 1.26 | 0.79 | 0.66 | 1.21 | 3.85 | 0.94 | 0.90 | 0.32 | 2.00 | 1.61 |
| 2.02 | 1 | 5 | 1.15 | 0.66 | 1.03 | 1.02 | 3.13 | 0.77 | 0.95 | 0.26 | 1.64 | 1.30 |
| 2.03 | 1 | 6 | 1.14 | 0.58 | 0.52 | 0.97 | 2.96 | 0.79 | 0.75 | 0.34 | 1.57 | 1.20 |
| 2.04 | 1 | 7 | 1.17 | 0.72 | 0.44 | 0.89 | 3.27 | 0.73 | 0.78 | 0.37 | 1.63 | 1.42 |
| 2.11 | 2 | 14 | 1.26 | 1.03 | 0.38 | 1.15 | 2.81 | 1.01 | 0.89 | 0.46 | 1.66 | 1.00 |
| 2.18 | 3 | 21 | 1.09 | 0.70 | 0.62 | 1.38 | 3.09 | 0.91 | 0.80 | 0.25 | 1.79 | 1.15 |
| 2.25 | 4 | 28 | 1.34 | 0.84 | 1.02 | 1.71 | 3.55 | 1.10 | 1.07 | 0.25 | 2.12 | 1.28 |
| 3.03 | 5 | 35 | 2.07 | 2.23 | 1.65 | 1.97 | 4.54 | 1.12 | 1.98 | 0.30 | 2.54 | 1.78 |
| 3.10 | 6 | 42 | 1.53 | 1.13 | 1.87 | 1.86 | 3.34 | 1.40 | 1.51 | 0.37 | 2.20 | 1.01 |
| 3.17 | 7 | 49 | 1.33 | 1.09 | 1.16 | 1.67 | 2.23 | 1.29 | 1.19 | 0.12 | 1.73 | 0.47 |
| 3.24 | 8 | 56 | 1.56 | 1.29 | 1.30 | 1.28 | 2.09 | 1.54 | 1.38 | 0.15 | 1.64 | 0.41 |
| 3.31 | 9 | 63 | 1.06 | 0.83 | 1.39 | 1.13 | 2.27 | 0.97 | 1.09 | 0.28 | 1.46 | 0.71 |
| 4.07 | 10 | 70 | 1.39 | 1.00 | 1.36 | 1.42 | 3.51 | 1.48 | 1.25 | 0.22 | 2.14 | 1.19 |
| 4.14 | 11 | 77 | 1.23 | 1.15 | 1.41 | 1.61 | 3.47 | 1.07 | 1.26 | 0.13 | 2.05 | 1.26 |
| 4.21 | 12 | 84 | 1.29 | 1.10 | 1.21 | 1.23 | 3.47 | 1.23 | 1.20 | 0.10 | 1.98 | 1.29 |
| 4.28 | 13 | 91 | 1.38 | 0.88 | 1.10 | 1.09 | 3.22 | 1.38 | 1.12 | 0.25 | 1.90 | 1.16 |
| 5.05 | 14 | 98 | 1.94 | 1.01 | 1.32 | 1.28 | 3.76 | 1.19 | 1.42 | 0.47 | 2.08 | 1.46 |
| 5.12 | 15 | 105 | 1.54 | 0.98 | 1.23 | 1.37 | 3.48 | 1.31 | 1.25 | 0.28 | 2.05 | 1.24 |
| 5.19 | 16 | 112 | 1.61 | 0.94 | 1.30 | 1.22 | 3.98 | 1.59 | 1.28 | 0.34 | 2.26 | 1.50 |
| 5.26 | 17 | 119 | 1.36 | 0.97 | 1.49 | 1.48 | 2.66 | 1.65 | 1.27 | 0.27 | 1.93 | 0.64 |
| 6.02 | 18 | 126 | 1.40 | 0.93 | 0.95 | 0.99 | 3.25 | 1.16 | 1.09 | 0.27 | 1.80 | 1.26 |
| 6.09 | 19 | 133 | 1.47 | 1.19 | 1.33 | 1.36 | 3.36 | 0.98 | 1.33 | 0.14 | 1.90 | 1.28 |
| 6.16 | 20 | 140 | 1.16 | 1.25 | 0.85 | 3.2* | 3.46 | 1.03 | 1.09 | 0.21 | 2.25 | 1.72 |
| 6.23 | 21 | 147 | 1.16 | 1.23 | 1.26 | 1.17 | 5.56 | 1.53 | 1.22 | 0.05 | 2.75 | 2.44 |
| 6.30 | 22 | 154 | 1.63 | 2.02* | 1.44 | 1.41 | 5.21 | 1.34 | 1.54 | 0.13 | 2.65 | 2.21 |
| 7.07 | 23 | 161 | 1.26 | 1.04 | 0.92 | 1.41 | 44.82** | 1.36 | 1.07 | 0.17 | 1.39 | 0.04 |
| 7.14 | 24 | 168 | 1.85 | 0.9 | BLQ | 1.5 | 3.78 | 1.26 | 1.38 | 0.67 | 2.18 | 1.39 |
| 7.21 | 25 | 175 | 1.69 | 1 | BLQ | 1.29 | 3.46 | 1.3 | 1.35 | 0.49 | 2.02 | 1.25 |
| 7.28 | 26 | 182 | 1.42 | 1.09* | 0.34 | 1.7 | 4.48 | 1.82 | 0.88 | 0.76 | 2.67 | 1.57 |

*re-analysis
**re-analysis, abnormal data

Figure 14:
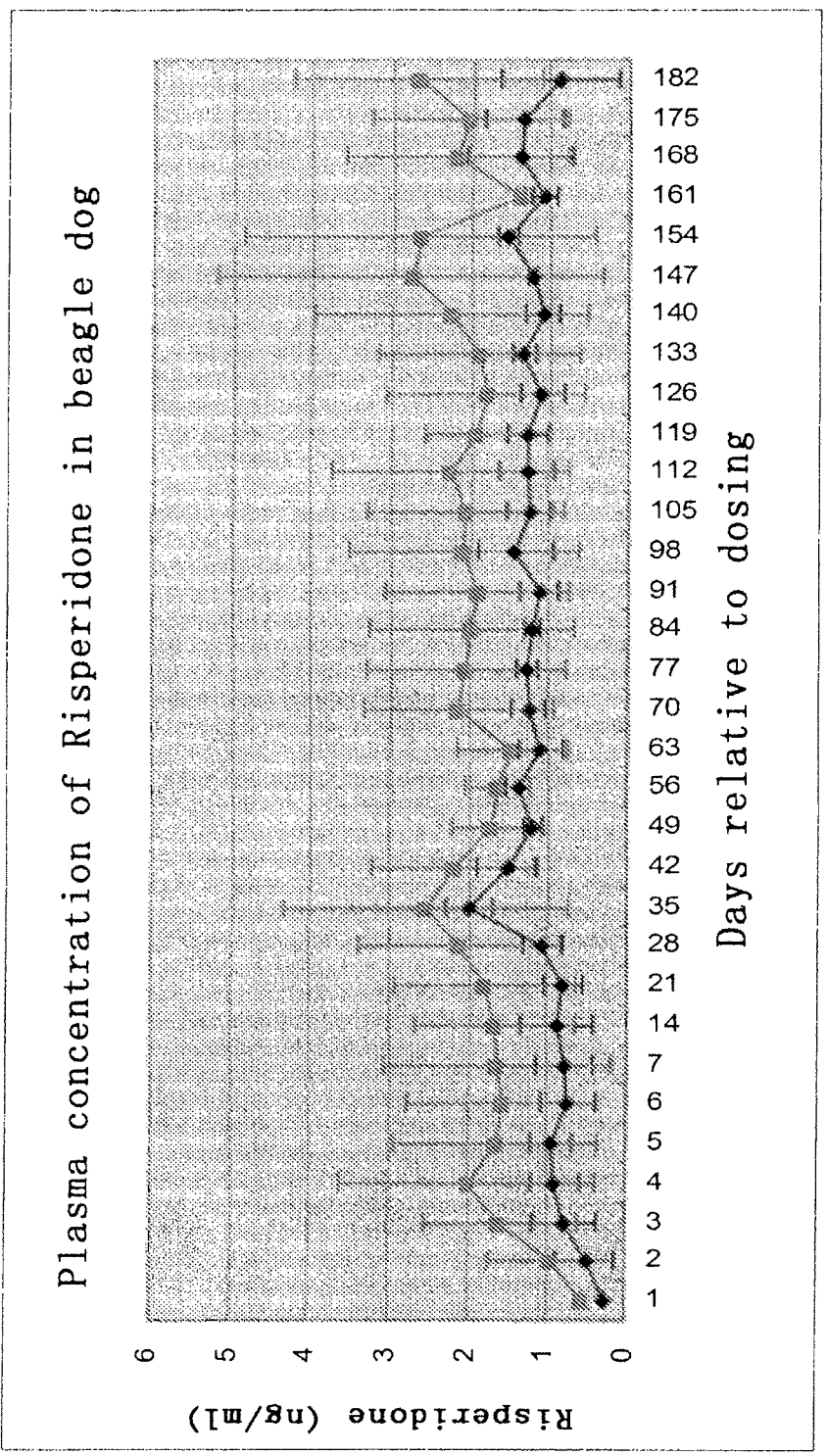
FIG. 14 is a graph of the in vivo plasma concentration of risperidone in the beagle dog study described in Example 8. The lower plot represents the average plasma concentration achieved in dogs implanted with one Carbothane® PC-3575A polyurethane implant (Flex Modulus 620 psi). The upper plot represents the average plasma concentration achieved in dogs implanted with two Carbothane® PC-3575A polyurethane implants (Flex Modulus 620 psi).

FIG. 14 is a graph of the in vivo plasma concentration of risperidone in the beagle dog study. The lower plot represents the average plasma concentration achieved in dogs implanted with one Carbothane® PC-3575A polyurethane implant (F.M. 620 psi). The upper plot represents the average plasma concentration achieved in dogs implanted with two Carbothane® PC-3575A polyurethane implants (F.M. 620 psi).

EQUIVALENTS

The present disclosure is not to be limited in terms of the particular embodiments described in this application, which are intended as illustrations of various aspects. Many modifications and variations can be made without departing from the spirit and scope of the disclosure, as will be apparent to those skilled in the art. Functionally equivalent methods, systems, and apparatus within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting. As will be understood by one skilled in the art, for any and all purposes, such as in terms of providing a written description, all ranges disclosed herein also encompass any and all possible subranges and combinations of subranges thereof.

While various aspects and embodiments have been disclosed herein, other aspects and embodiments will be apparent to those skilled in the art. All references cited herein are incorporated by reference in their entireties.

What is claimed is:

1. An implantable drug delivery device, comprising a polyurethane-based polymer having polyether-based polyol segments represented by the formula $-[O-(CH_2)_n]_x-O-$, said polyurethane-based polymer configured to provide a cylindrically shaped reservoir, wherein the reservoir is sealed after being charged with an effective amount of solid formulation comprising an active agent and one or more pharmaceutically acceptable carriers, such that the release of the active agent at a substantially zero order rate in vitro by diffusion through the polyurethane-based polymer generally increases as the equilibrium water content (% EWC) of the polymer increases, wherein the active agent is histrelin, risperidone, dexamethasone, naltrexone, metolazone, clonidine, or selegiline.

2. The drug delivery device of claim 1, wherein the active agent is histrelin.

3. The drug delivery device of claim 1, wherein the active agent is risperidone.

4. The drug delivery device of claim 1, wherein the active agent is dexamethasone.

5. The drug delivery device of claim 1, wherein the active agent is naltrexone.

6. The drug delivery device of claim 1, wherein the active agent is metolazone.

7. The drug delivery device of claim 1, wherein the active agent is clonidine.

8. The drug delivery device of claim 1, wherein the active agent is selegiline.

9. The drug delivery device of claim 1, wherein the polyurethane-based polymer has a % EWC of between about 5%-43%.

10. The drug delivery device of claim 1, wherein the one or more pharmaceutically acceptable carriers is selected from the group consisting of croscarmellose, stearic acid, and a combination thereof.

11. The drug delivery device of claim 10, wherein the one or more pharmaceutically acceptable carriers are croscarmellose and stearic acid.

12. The drug delivery device of claim 11, wherein the croscarmellose comprises 10% of the solid drug formulation, and stearic acid comprises 2% of the solid drug formulation.

13. The drug delivery device of claim 1, wherein the reservoir has a wall thickness of 0.2 mm.

14. A method of delivering an active agent to a subject, comprising implanting an implantable device into the subject, wherein the implantable device comprises a polyurethane-based polymer having polyether-based polyol segments represented by the formula $-[O-(CH_2)_n]_x-O-$, said polyurethane-based polymer configured to provide a cylindrically shaped reservoir, wherein the reservoir is sealed after being charged with an effective amount of solid formulation comprising an active agent and one or more pharmaceutically acceptable carriers, such that the release of the active agent at a substantially zero order rate in vitro by diffusion through the polyurethane-based polymer generally increases as the equilibrium water content (% EWC) of the polymer increases, wherein the active agent is histrelin, risperidone, dexamethasone, naltrexone, metolazone, clonidine, or selegiline.

15. The method of claim 14, wherein the active agent is histrelin.

16. The method of claim 14, wherein the active agent is risperidone.

17. The method of claim 14, wherein the active agent is dexamethasone.

18. The method of claim 14, wherein the active agent is naltrexone.

19. The method of claim 14, wherein the active agent is metolazone.

20. The method of claim 14, wherein the active agent is clonidine.

21. The method of claim 14, wherein the active agent is selegiline.

22. The method of claim 14, wherein the polyurethane-based polymer has a % EWC of between about 5%-43%.

23. The method of claim 14, wherein the one or more pharmaceutically acceptable carriers is selected from the group consisting of croscarmellose, stearic acid, and a combination thereof.

24. The method of claim 23, wherein the one or more pharmaceutically acceptable carriers are croscarmellose and stearic acid.

25. The method device of claim 24, wherein the croscarmellose comprises 10% of the solid drug formulation, and stearic acid comprises 2% of the solid drug formulation.

26. The method of claim 14, wherein the reservoir has a wall thickness of 0.2 mm.

27. A process for manufacturing a drug delivery device comprising: supplying a polyurethane-based polymer formed as a hollow tube; loading a solid formulation comprising one or more active ingredients into the tube; and sealing the tube; wherein the one or more active ingredients and the polyurethane-based polymer are selected such that either: (i) both the one or more active ingredients and the polyurethane-based polymer exhibit hydrophilic characteristics, or (ii) both the one or more active ingredients and the polyurethane-based polymer exhibit hydrophobic characteristics; and wherein the drug delivery device delivers the one or more active ingredients by diffusion through the polyurethane-based polymer at a substantially zero order release rate in vitro and wherein the polyurethane-based polymer is formed from one or more polyols, wherein the general polyol structure is selected from the group consisting of:

—[O—(CH$_2$)$_n$]$_x$—O—;

O—(CH$_2$—CH$_2$—CH$_2$—CH$_2$)$_x$—O—; and

O—[(CH$_2$)$_6$—CO$_3$]$_n$—(CH$_2$)—O—.

28. The process of claim 27, wherein the sealing of the hollow tube comprises inserting a pre-fabricated plug into an open end and applying heat or solvent to the pre-fabricated plug and polyurethane-based polymer.

29. The process of claim 27, wherein the sealing comprises inserting a pre-fabricated end plug at an open end of the hollow tube; applying an appropriate light-initiated and/or heat-initiated thermoset polyurethane formulation into an interface formed between the pre-fabricated end plug and the open end; and curing the polyurethane formulation with light and/or heat to seal the pre-fabricated plug in the end of the tube.

30. The process of claim 27 further comprising conditioning and priming comprises selecting a parameter selected from the group consisting of time, temperature, and medium to influence the substantially zero order release rate in vitro of the one or more active ingredients through the polyurethane-based polymer.

31. The process of claim 27, wherein the one or more active ingredients and the polyurethane-based polymer are selected such that both the one or more active ingredients and the polyurethane-based polymer exhibit hydrophilic characteristics.

32. The process of claim 27, wherein the one or more active ingredients and the polyurethane-based polymer are selected such that both the one or more active ingredients and the polyurethane-based polymer exhibit hydrophobic characteristics.

33. The process of claim 27, wherein the solid formulation includes one or more pharmaceutically acceptable carriers that are not required for the substantially zero order release rate in vitro of the one or more active ingredients through the polyurethane-based polymer.

34. The process of claim 33, wherein the one or more pharmaceutically acceptable carriers are not required for the substantially zero order release rate in vitro of the one or more active ingredients as governed by Fick's Law of Diffusion.

35. The process of claim 27, wherein the hollow tube is formed by extrusion molding, injection molding, or spin-casting of the polyurethane-based polymer.

36. The process of claim 27, wherein the hollow tube is formed with two open ends.

37. The process of claim 27, wherein the hollow tube is formed with two open ends, and one end is sealed prior to the loading.

38. The process of claim 27, wherein the hollow tube is formed with one open end and one closed end.

39. The process of claim 31 in which the at least one active ingredient is selected from drugs that can act on the central nervous system, psychic energizers, tranquilizers, anti-convulsants, muscle relaxants, anti-parkinson, analgesic, anti-inflammatory, anesthetic, antispasmodic, muscle contractants, anti-microbials, anti-malarials, hormonal agents, sympathomimetic, cardiovascular, diuretics, and antiparasitic.

40. The process of claim 32 in which the at least one active ingredient is selected from drugs that can act on the central nervous system, psychic energizers, tranquilizers, anti-convulsants, muscle relaxants, anti-parkinson, analgesic, anti-inflammatory, anesthetic, antispasmodic, muscle contractants, anti-microbials, anti-malarials, hormonal agents, sympathomimetic, cardiovascular, diuretics, and antiparasitic.

41. The process of claim 27, wherein the at least one active ingredient is selected from the group consisting of histrelin, risperidone, dexamethasone, naltrexone, metolazone, clonidine, and selegiline.

* * * * *